(12) United States Patent
Nokami et al.

(10) Patent No.: US 12,404,293 B2
(45) Date of Patent: Sep. 2, 2025

(54) METHOD FOR PRODUCING GLYCAN, BUILDING BLOCK FOR GYLICAN SYNTHESIS, AND COMPOUND

(71) Applicants: NATIONAL UNIVERSITY CORPORATION TOTTORI UNIVERSITY, Tottori (JP); KOGANEI CORPORATION, Tokyo (JP)

(72) Inventors: Toshiki Nokami, Tottori (JP); Toshiyuki Itoh, Tottori (JP); Hiraku Sakai, Tokyo (JP); Tomoaki Hamada, Tokyo (JP)

(73) Assignees: NATIONAL UNIVERSITY CORPORATION TOTTORI UNIVERSITY, Tottori (JP); KOGANEI CORPORATION, Tokyo (JP)

( * ) Notice: Subject to any disclaimer, the term of this patent is extended or adjusted under 35 U.S.C. 154(b) by 976 days.

(21) Appl. No.: 17/434,331

(22) PCT Filed: Feb. 25, 2020

(86) PCT No.: PCT/JP2020/007365
§ 371 (c)(1),
(2) Date: Mar. 11, 2022

(87) PCT Pub. No.: WO2020/175440
PCT Pub. Date: Sep. 3, 2020

(65) Prior Publication Data
US 2023/0143273 A1    May 11, 2023

(30) Foreign Application Priority Data

Feb. 28, 2019  (JP) .................................. 2019-035709

(51) Int. Cl.
C07H 3/06        (2006.01)
C07D 309/04      (2006.01)
C07H 3/02        (2006.01)

(52) U.S. Cl.
CPC ............. *C07H 3/06* (2013.01); *C07D 309/04* (2013.01); *C07H 3/02* (2013.01)

(58) Field of Classification Search
None
See application file for complete search history.

(56) References Cited

FOREIGN PATENT DOCUMENTS

JP      2017-165725 A      9/2017
WO     WO-2019075045 A1  *  4/2019  ............... A61P 1/16

OTHER PUBLICATIONS

Yang et al., Tetrahedron Letters, vol. 53(39), pp. 5231-5234, 2012. (Year: 2012).*
Nokami et al. (Organic Letters, 2015, vol. 17(6), pp. 1525-1528. (Year: 2015).*
Japanese Notice of Reasons for Refusal for corresponding Japanese Application No. 2019-035709, dated Feb. 28, 2023, with an English translation.
Alvarez-Mico et al., "A new glycosidation method through nitrate displacement on substituted nitrobenzenes," Carbohydrate Research, vol. 342, No. 3-4, 2007 (Available online Nov. 21, 2006), pp. 440-447.
Feng et al., "Synthesis of a Forssman antigen derivative for use in a conjugate vaccine," Carbohydrate Research, vol. 346, No. 17, 2011 (Available online Sep. 29, 2011), pp. 2650-2662.
International Preliminary Report on Patentability and English translation of the Written Opinion of the International Searching Authority (Forms PCT/IB/373 and PCT/ISA/237) for International Application No. PCT/JP2020/007365, dated Aug. 25, 2021.
Kumar et al., "Application of Halide Molten Salts as Novel Reaction Media for O-Glycosidic Bond Formation," European Journal of Organic Chemistry, vol. 18, 2010 (Available online May 11, 2010), pp. 3377-3381.
Li et al., "Mechanistic Studies and Methods to Prevent Aglycon Transfer of Thioglycosides," Journal of the American Chemical Society, vol. 128, No. 35, 2006 (Available online Aug. 15, 2006), pp. 11612-11619.
Li et al., "Thio-arylglycosides with various aglycon para-substituents: a probe for studying chemical glycosylation reactions," Organic & Biomolecular Chemistry, vol. 7, No. 1, 2009, pp. 117-127.
Narine et al., "Mechanistic Requirements for the Efficient Enzyme-Catalyzed Hydrolysis of Thiosialosides," Biochemistry, vol. 45, No. 30, 2006 (Available online Jul. 11, 2006), pp. 9319-9326.
Nokami et al., "Automated Electrochemical Assembly of the Protected Potential TMG-chitotriomycin Precursor Based on Rational Optimization of the Carbohydrate Building Block," Organic Letters, vol. 17, No. 6. Mar. 10, 2015, pp. 1525-1528.
Nokami et al., "Automated Solution-Phase Synthesis of Oligosaccharides via Iterative Electrochemical Assembly of Thioglycosides," Organic Letters, vol. 15, No. 17, 2013 (Available online Aug. 15, 2013), pp. 4520-4523.
Nokami et al., Electrochemistry, vol. 83, No. 6, Jun. 5, 2015, pp. 472-476.

(Continued)

*Primary Examiner* — Traviss C McIntosh, III
(74) *Attorney, Agent, or Firm* — Birch, Stewart, Kolasch & Birch, LLP

(57) ABSTRACT

This invention provides a method for producing a glycan with improved yield ratio of streocontrolled glycan. Additionally it provides the building blocks used as the sugar donor and as the sugar acceptor to implement a method for producing the glycan. It also provides a novel compound. It subjects the specific building block A of this invention to electrolytic oxidation in an aprotic organic solvent that contains an electrolyte; and subjects the specific building block B of this invention to glycosylation with the electrolytically oxidized building block A in the method for producing a glycan based on the liquid phase process.

13 Claims, 1 Drawing Sheet

(56) References Cited

OTHER PUBLICATIONS

Wu et al., "Synthesis of Monomeric and Dimeric Repeating Units of the Zwitterionic Type 1 Capsular Polysaccharide from *Streptococcus* pneumoniae," Chemistry-A European Journal, vol. 16, No. 11, 2010 (Available online Feb. 9, 2010), pp. 3476-3488.

Xie et al., "Enzymatic N-Glycosylation of Diverse Arylamine Aglycones by a Promiscuous Glycosyltransferase from Carthamus tinctorius," Advanced Synthesis & Catalysis, vol. 359, No. 4, 2017 (Available online Jan. 18, 2017), pp. 603-608.

Zhang et al., "Total synthesis of LeA-LacNAc pentasaccharide as a ligand for Clostridium difficile toxin A." Organic & Biomolecular Chemistry, vol. 8, No. 1, 2010, pp. 128-136.

Extended European Search Report for corresponding European Application No. 20763290.2, dated Nov. 15, 2022.

\* cited by examiner

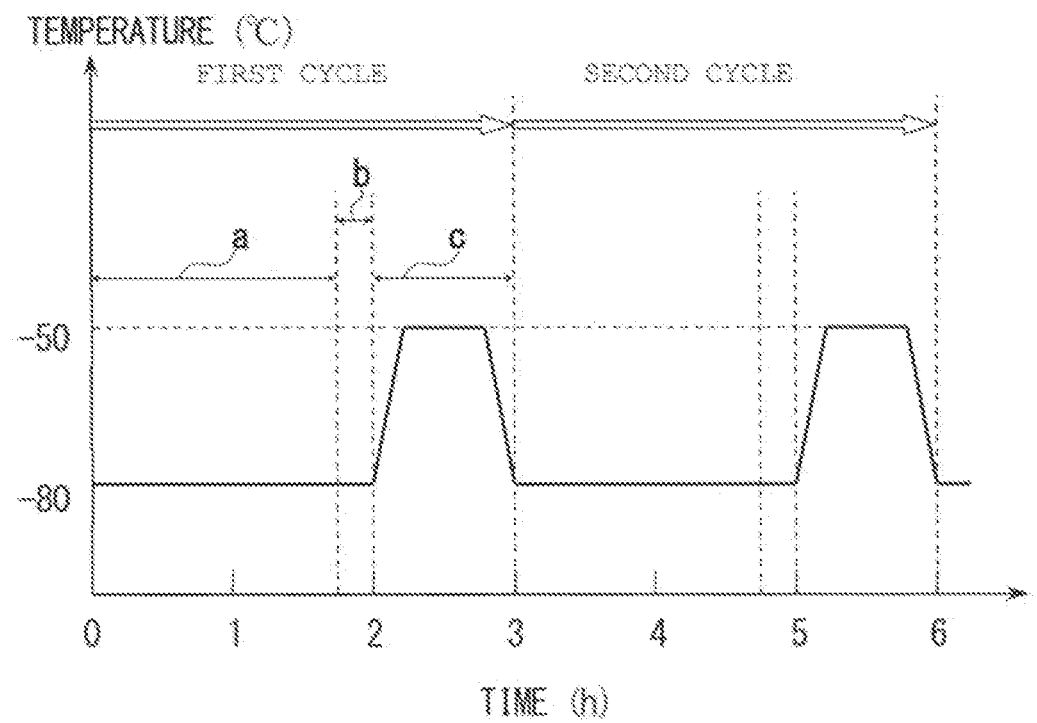

METHOD FOR PRODUCING GLYCAN, BUILDING BLOCK FOR GYLICAN SYNTHESIS, AND COMPOUND

TECHNICAL FIELD

This invention relates to a method for producing a glycan, a building block for glycan synthesis, and a compound.

BACKGROUND ART

In the fields of nutritional supplementary food (supplement), medicine and agricultural chemical, public attention has been focused on functionality of oligosaccharide (saccharide composed of two to ten and several monosaccharides bound through glycosidic bond). For example in the field of nutritional supplementary food, the oligosaccharide is applicable in expectation of use of its physiological functions for intestinal regulation (effect for improving intestinal flora), promotion of mineral absorption, anticariogenecity, antiallergic and immunostimulation. Meanwhile in the fields of medicine and agricultural chemical, the oligosaccharide is expected as an active ingredient per se, or as a lead compound in drug design. The oligosaccharide, when intended for use as such functional compound, is synthesized essentially under control of stereoselectivity, that is, while forming the glycosidic bond with a desired stereochemistry. Control of the stereoselectivity, if enabled, will make separation and purification of isomers no longer necessary, or make them easier.

Synthesis of oligosaccharide is roughly classified into solid phase process and liquid phase process, wherein the liquid phase process have a number of industrial advantages including easiness of scaling-up, and, unnecessity of separation from a carrier.

Hence, there is a desire for a synthetic method of oligosaccharide based on the liquid phase process with high stereoselectivity.

For example, Patent Literature 1, Non-Patent Literature 1 and Non-Patent Literature 2 describe methods for producing an oligosaccharide, by which a sugar donor is electrochemically oxidized in an electrolytic solution, thereby allowing a glycosilation reaction to proceed. More specifically, these methods described in the literatures include subjecting a sugar donor to low-temperature electrolytic oxidation in the presence of tetrabutylammonium triflate ($Bu_4NOTf$) to produce, and then accumulate, a glycosyl trifulate which is an important intermediate for glycosylation reaction; then subjecting the intermediate and the sugar acceptor to glycosylation; and then deblocking the thus glycosylated oligosaccharide precursor. The literatures describe that such methods can efficiently produce the oligosaccharide with high stereoselectivity, and are also useful for automated synthesis.

CITATION LIST

Patent Literature

[Patent Literature 1] JP 2017-165725 A

Non-Patent Literature

[Non-Patent Literature 1] Toshiki Nokami, et al., Organic Letters, 2015, Vol. 17, No. 6, pp. 1525-1528
[Non-Patent Literature 2] Toshiki Nokami, et al., Organic Letters, 2013, Vol. 15, No. 17, pp. 4520-4523

SUMMARY OF THE INVENTION

Technical Problem

Although the methods described in Patent Literature 1, Non-Patent Literature 1 and Non-Patent Literature 2 have improved yield ratio of streocontrolled oligosaccharide in the oligosaccharide synthesis based on the liquid phase process, there is still a need for further improvement in the yield ratio.

This invention was arrived at in consideration of the aforementioned problem, aiming at providing a method for producing a glycan with improved yield ratio of streocontrolled glycan.

It is another object of this invention to provide a building block for glycan synthesis used for the aforementioned production method. It is still another object of this invention to provide a novel compound.

Solution to Problem

The problems described above could be solved by controlling electron density on glycosidic bond between the sugar donor and the sugar acceptor and suppressing the side reactions. Specifically, the problems described above are solved by the following means <1>, and preferably by the following means <2> below.

<1> A method for producing a glycan, the method comprising:
subjecting a building block A, which is at least one building block selected from a building block represented by Formula (1) below, or a building block that contains a sugar residue derived from the building block represented by Formula (1) below and a sugar residue derived from a building block represented by Formula (2) below, to electrolytic oxidation in an aprotic organic solvent that contains an electrolyte; and
subjecting a building block B, which is at least one building block selected from a building block represented by Formula (2) below, or a building block that contains a plurality of sugar residues derived from the building block represented by Formula (2), to glycosylation with the electrolytically oxidized building block A:

Formula (1)

[Chemical Formula 1]

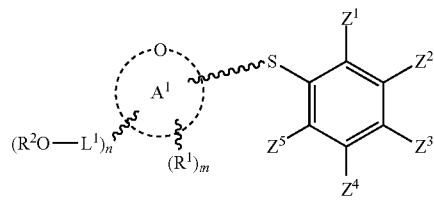

in Formula (1),
$A^1$ represents a cyclic structure having 4 to 8 carbon atoms;
each of $Z^1$ to $Z^5$ independently represents a hydrogen atom or an electron attractive group, with the total of the Hammett's σ values of $Z^1$ to $Z^5$ exceeding 0.12;
$L^1$ represents a single bond or a divalent linking group;
each of $R^1$ and $R^2$ independently represents a monovalent organic group;

each of m ($R^1$)s and n ($R^2$)s may bind to each other to form a ring;

m represents an integer of 0 or larger, n represents an integer of 1 or larger;

m+n is equal to or smaller than the number of carbon atoms of the cyclic structure $A^1$;

each wavy line independently represents a bond in the equatorial or axial conformation;

[Chemical Formula 2]

Formula (2)

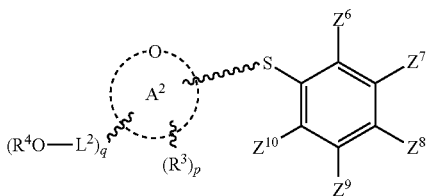

in Formula (2), $A^2$ represents a cyclic structure having 4 to 8 carbon atoms;

each of $Z^6$ to $Z^{10}$ independently represents a hydrogen atom or an electron attractive group, with the total of the Hammett's σ values of $Z^6$ to $Z^{10}$ exceeding 0.12;

$L^2$ represents a single bond or a divalent linking group;

$R^3$ represents a monovalent organic group, $R^4$ represents a hydrogen atom or a monovalent organic group, at least one of q ($R^4$)s represents a hydrogen atom;

each of p ($R^3$)s and q ($R^4$)s may bind to each other to form a ring;

p represents an integer of 0 or larger, q represents an integer of 1 or larger;

p+q is equal to or smaller than the number of carbon atoms of the cyclic structure $A^2$; and each wavy line independently represents a bond in the equatorial or axial conformation.

<2> The production method of <1>, wherein the total of the Hammett's σ values of $Z^1$ to $Z^5$ is 0.2 or larger, with the total of the Hammett's σ values of $Z^6$ to $Z^{10}$ is 0.2 or larger.

<3> The production method of <1> or <2>, wherein the total of the Hammett's σ values of $Z^1$ to $Z^5$ is 1.5 or smaller, with the total of the Hammett's σ values of $Z^6$ to $Z^{10}$ is 1.5 or smaller.

<4> The production method of any one of <1> to <3>, wherein at least one of $Z^1$ to $Z^{10}$ represents a halogen atom.

<5> The production method of <4>, wherein at least one of $Z^1$ to $Z^5$ represents a halogen atom, and at least one of $Z^6$ to $Z^{10}$ represents a halogen atom.

<6> The production method of <5>, wherein any two of $Z^1$ to $Z^5$ represent halogen atoms, and the other represent hydrogen atoms, and any two of $Z^6$ to $Z^{10}$ represent halogen atoms, and the other represent hydrogen atoms.

<7> The production method of <5>, wherein one of $Z^1$ to $Z^5$ represents a halogen atom, and the other represent hydrogen atoms, and one of $Z^6$ to $Z^{10}$ represents a halogen atom, and the other represent hydrogen atoms.

<8> The production method of any one of <4> to <7>, wherein the halogen atom is at least one of chlorine atom or bromine atom.

<9> The production method of any one of <1> to <8>, wherein a building block represented by Formula (1-2) below is used as the building block represented by Formula (1);

[Chemical Formula 3]

Formula (1-2)

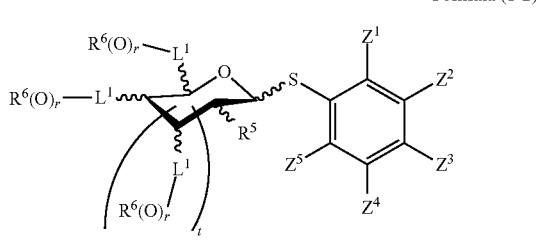

in Formula (1-2), each of $Z^1$ to $Z^5$ independently represents a hydrogen atom or an electron attractive group, with the total of the Hammett's σ values of $Z^1$ to $Z^5$ exceeding 0.12;

each $L^1$ independently represents a single bond or a divalent linking group;

each of $R^5$ and $R^6$ independently represents a monovalent organic group;

$R^5$ and $R^6$ may bind to each other to form a ring, t represents an integer from 0 to 4;

each r independently represents 0 or 1; and each wavy line independently represents a bond in the equatorial or axial conformation.

<10> The production method of <9>, wherein t represents 0 or 1.

<11> The production method of any one of <1> to <10>, wherein a building block represented by Formula (2-2) below is used as the building block represented by Formula (2);

[Chemical Formula 4]

Formula (2-2)

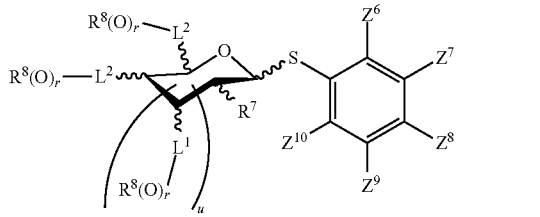

in Formula (2-2), each of $Z^6$ to $Z^{10}$ independently represents a hydrogen atom or an electron attractive group, with the total of the Hammett's σ values of $Z^6$ to $Z^{10}$ exceeding 0.12;

$R^7$ represents a monovalent organic group, each $R^8$ independently represents a hydrogen atom or a monovalent organic group;

$R^7$ and $R^8$ may bind to each other to form a ring, u represents an integer from 0 to 4;

each r independently represents 0 or 1;

at least one $R^8(O)_r$ represents a hydroxy group; and each wavy line independently represents a bond in the equatorial or axial conformation.

<12> The production method of <11>, wherein u represents 0 or 1.

<13> The production method of any one of <1> to <12>, wherein at least one of the building block A or the building block B is a disaccharide, thereby obtaining a polysaccharide equal to longer than trisaccharide as a deliverable.

<14> A building block used in glycan synthesis represented by Formula (1) below, or, contains a sugar residue derived from the building block represented by Formula (1) below:

[Chemical Formula 5]

Formula (1)

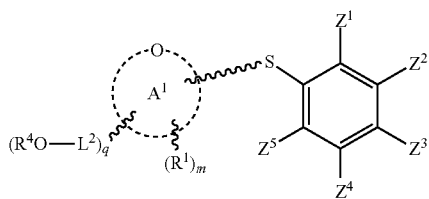

in Formula (1), $A^1$ represents a cyclic structure having 4 to 8 carbon atoms;

each of $Z^1$ to $Z^5$ independently represents a hydrogen atom or an electron attractive group, with the total of Hammett's σ values of $Z^1$ to $Z^5$ exceeding 0.12;

$L^1$ represents a single bond or a divalent linking group;

each of $R^1$ and $R^2$ independently represents a monovalent organic group;

each of m ($R^1$)s and n ($R^2$)s may bind to each other to form a ring;

m represents an integer of 0 or larger, n represents an integer of 1 or larger;

m+n is equal to or smaller than the number of carbon atoms of the cyclic structure $A^1$; and each wavy line independently represents a bond in the equatorial or axial conformation.

<15> A building block used in glycan synthesis represented by Formula (2) below, or, contains a sugar residue derived from the building block represented by Formula (2) below:

[Chemical Formula 6]

Formula (2)

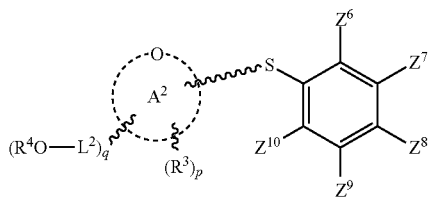

in Formula (2), $A^2$ represents a cyclic structure having 4 to 8 carbon atoms;

each of $Z^6$ to $Z^{10}$ independently represents a hydrogen atom or an electron attractive group, with the total of the Hammett's σ values of $Z^6$ to $Z^{10}$ exceeding 0.12;

$L^2$ represents a single bond or a divalent linking group;

$R^3$ represents a monovalent organic group, $R^4$ represents a hydrogen atom or a monovalent organic group, and at least one of q ($R^4$)s represents a hydrogen atom;

each of p ($R^3$)s and q ($R^4$)s may bind to each other to form a ring;

p represents an integer of 0 or larger, q represents an integer of 1 or larger;

p+q is equal to or smaller than the number of carbon atoms of the cyclic structure $A^2$; and each wavy line independently represents a bond in the equatorial or axial conformation.

<16> A compound represented by Formula (3) below:

[Chemical Formula 7]

Formula (3)

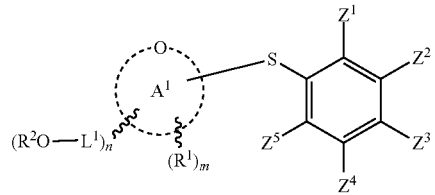

in Formula (3), $A^1$ represents a cyclic structure having 4 to 8 carbon atoms;

each of $Z^1$ to $Z^5$ independently represents a hydrogen atom or an electron attractive group, with the total of the Hammett's σ values of $Z^1$ to $Z^5$ exceeding 0.12;

$L^1$ represents a single bond or a divalent linking group;

$R^1$ represents a phthalimido group, azido group, amido group, alkyl group, $-[O(CH_2)_i]_j-OC_kH_{2k+1}$ (where, i represents an integer from 1 to 10, j represents an integer from 0 to 5, k represents an integer from 1 to 10), $-[O(CH_2)_i]_j-OC_kH_{2k-1}$ (where, i represents an integer from 1 to 10, j represents an integer from 0 to 5, k represents an integer from 2 to 10), $-O-C(=O)-C_kH_{2k+1}$ (where, k represents an integer from 1 to 10), $-O(CH_2)_i-Ar$ (where, i represents an integer from 1 to 10, Ar represents an aryl group having 6 to 10 carbon atoms), $-O-C(=O)-Ar$ (where, Ar represents an aryl group having 6 to 10 carbon atoms) or alkylsiloxy group, $R^2$ represents an alkyl group, $-[(CH_2)_iO]_j-C_kH_{2k+1}$ (where, i represents an integer from 1 to 10, j represents an integer from 1 to 5, k represents an integer from 1 to 10), $-C(=O)-C_kH_{2k+1}$ (where, k represents an integer from 1 to 10), $-(CH_2)_i-Ar$ (where, i represents an integer from 1 to 10, Ar represents an aryl group having 6 to 10 carbon atoms), $-C(=O)-Ar$ (where, Ar represents an aryl group having 6 to 10 carbon atoms);

each of m ($R^1$)s and n ($R^2$)s may bind to each other to form a ring;

m represents an integer of 0 or larger, n represents an integer of 1 or larger;

m+n is equal to or small than the number of carbon atoms of the cyclic structure $A^1$;

each wavy line independently represents a bond in the equatorial or axial conformation; and a bond between $A^1$ and S is in the equatorial conformation.

<17> A compound represented by Formula (4) below:

[Chemical Formula 8]

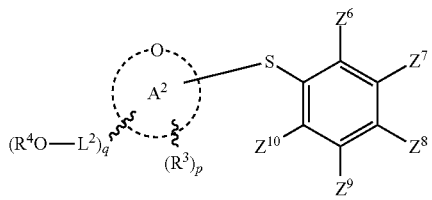

Formula (4)

in Formula (4), $A^2$ represents a cyclic structure having 4 to 8 carbon atoms;

each of $Z^6$ to $Z^{10}$ independently represents a hydrogen atom or an electron attractive group, with the total of the Hammett's σ values of $Z^6$ to $Z^{10}$ exceeding 0.12;

$L^2$ represents a single bond or a divalent linking group;

$R^3$ represents a phthalimido group, azido group, amido group, alkyl group, $-[O(CH_2)_i]_j-OC_kH_{2k+1}$ (where, i represents an integer from 1 to 10, j represents an integer from 0 to 5, k represents an integer from 1 to 10), $-[O(CH_2)_i]_j-OC_kH_{2k-1}$ (where, i represents an integer from 1 to 10, j represents an integer from 0 to 5, k represents an integer from 2 to 10), $-O-C(=O)-C_kH_{2k+1}$ (where, k represents an integer from 1 to 10), $-O(CH_2)_i-Ar$ (where, i represents an integer from 1 to 10, Ar represents an aryl group having 6 to 10 carbon atoms), $-O-C(O)-Ar$ (where, Ar represents an aryl group having 6 to 10 carbon atoms) or alkylsiloxy group;

$R^4$ represents a hydrogen atom, alkyl group, $-[(CH_2)_i O]_j-C_kH_{2k+1}$ (where, i represents an integer from 1 to 10, j represents an integer from 1 to 5, k represents an integer from 1 to 10), $-C(=O)-C_kH_{2k+1}$ (where, k represents an integer from 1 to 10), $-(CH_2)_i-Ar$ (where, i represents an integer from 1 to 10, Ar represents an aryl group having 6 to 10 carbon atoms), $-C(=O)-Ar$ (where, Ar represents an aryl group having 6 to 10 carbon atoms), at least one of q ($R^4$)s represents a hydrogen atom;

each of p ($R^3$)s and q ($R^4$)s may bind to each other to form a ring;

p represents an integer of 0 or larger, q represents an integer of 1 or larger;

p+q is equal to or smaller than the number of carbon atoms of the cyclic structure $A^2$;

each wavy line independently represents a bond in the equatorial or axial conformation; and a bond between $A^2$ and S is in the equatorial conformation.

<18> A compound represented by Formula (5) below:

[Chemical Formula 9]

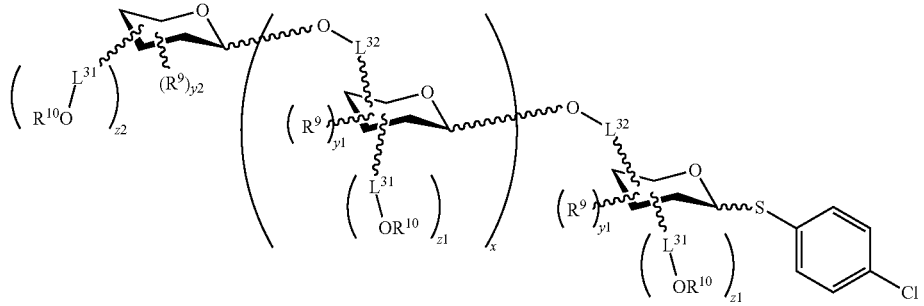

Formula (5)

in Formula (5), each of $L^{31}$ and $L^{32}$ independently represents a single bond, methylene group or ethylene group;

each $R^9$ independently represents a phthalimido group, azido group, acetyloxy group, acetamido group, benzyloxy group or benzoyloxy group;

each $R^{10}$ independently represents a hydrogen atom, methyl group, ethyl group, acetyl group, trimethylacetyl group, benzyl group or benzoyl group;

x represents an integer from 0 to 10;

each of y1 and y2 independently represents an integer from 0 to 2, each z1 independently represents an integer of 2 or 3;

z2 represents an integer from 2 to 4;

y1+z1=3, and, y2+z2=4 hold; and each wavy line independently represents a bond in the equatorial or axial conformation.

Advantageous Effects of Invention

The method for producing a glycan of this invention can improve the yield ratio of the streocontrolled glycan in the synthesis of oligosaccharide based on the liquid phase process, than in the prior methods. The building block of this invention enables implementation of the production method of this invention. Further, the compound of this invention can provide a novel material.

BRIEF DESCRIPTION OF DRAWING

FIG. 1 is a graph illustrating a part of a synthetic sequence in an embodiment of this invention.

DESCRIPTION OF EMBODIMENTS

Major embodiments of this invention will be explained below. Note, however, that this invention is by no means limited by the embodiments explicitly illustrated here.

All numerical ranges given in this patent specification, using "to" preceded and succeeded by numerals, are used to represent the ranges including these numerals respectively as the lower and upper limit values.

In this patent specification, the term "step" means not only an independent step, but also means a step which is not clearly discriminable from other steps, as long as an expected operation of such step can be achieved.

All notations for groups (atomic groups) without discrimination between substituted and non-substituted encompass groups free of substituent, as well as groups having substituent. For example, "alkyl group" simply notified like this encompasses both of alkyl group free of substituent (non-substituted alkyl group), and, alkyl group having substituent (substituted alkyl group). Non-substituted groups are preferred in this invention, unless otherwise specifically noted. In addition, "alkyl group" simply notified like this may either be chain-like or cyclic, and if chain-like, may either be straight chain-like or branched. The same will apply to "alkenyl group", "alkylene group" and "alkenylene group".

In this patent specification, Ar represents aryl group, Bu represents butyl group, Ph represents phenyl group, Me represents methyl group, Et represents ethyl group, TfO or OTf represents triflate group, Bn represents benzyl group, Ac represents acetyl group, Phth represents phthaloyl group, and MOM represents methoxymethyl group.

In this patent specification, all numerical ranges such as in "$C_{1-10}$" represent possible numbers of carbon atoms in hydrocarbon chains. For example, the notation "$C_{1-10}$ alkyl group" means an alkyl group having 1 to 10 carbon atoms. The same will apply to other hydrocarbon groups.

<Method for Producing Glycan>

The method for producing a glycan of this invention includes:

subjecting a building block A, which is at least one building block selected from a building block represented by Formula (1) below, or a building block that contains a sugar residue derived from the building block represented by Formula (1) below and a sugar residue derived from a building block represented by Formula (2) below, to electrolytic oxidation in an aprotic organic solvent that contains an electrolyte; and subjecting a building block B, which is at least one building block selected from a building block represented by Formula (2) below, or a building block that contains a plurality of sugar residues derived from the building block represented by Formula (2), to glycosylation with the electrolytically oxidized building block A.

[Chemical Formula 10]

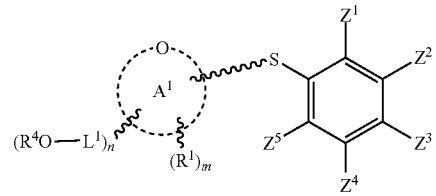

Formula (1)

In Formula (1), $A^1$ represents a cyclic structure having 4 to 8 carbon atoms, each of $Z^1$ to $Z^5$ independently represents a hydrogen atom or an electron attractive group, with the total of the Hammett's σ values of $Z^1$ to $Z^5$ exceeding 0.12, $L^1$ represents a single bond or a divalent linking group, each of $R^1$ and $R^2$ independently represents a monovalent organic group, each of m ($R^1$)s and n ($R^2$)s may bind to each other to form a ring, m represents an integer of 0 or larger, n represents an integer of 1 or larger, m+n is equal to or smaller than the number of carbon atoms of the cyclic structure $A^1$, and each wavy line independently represents a bond in the equatorial or axial conformation. Note that, from among the bonds of constituent atoms of the cyclic structure $A^1$, all bonds that neither form a ring nor bond with any of sulfur atom S, $R^1$ or $L^1$, are prescribed to have hydrogen atoms bound thereto.

Formula (2)

[Chemical Formula 11]

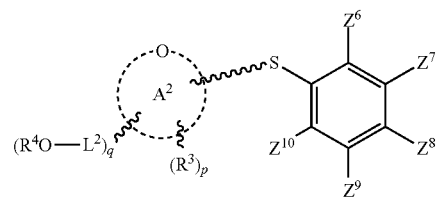

In Formula (2),

A² represents a cyclic structure having 4 to 8 carbon atoms;

each of $Z^6$ to $Z^{10}$ independently represents a hydrogen atom or an electron attractive group, with the total of the Hammett's σ values of $Z^6$ to $Z^{10}$ exceeding 0.12;

$L^2$ represents a single bond or a divalent linking group;

$R^3$ represents a monovalent organic group;

$R^4$ represents a hydrogen atom or a monovalent organic group, at least one of q ($R^4$)s represents a hydrogen atom;

each of p ($R^3$)s and q ($R^4$)s may bind to each other to form a ring;

p represents an integer of 0 or larger, q represents an integer of 1 or larger;

p+q is equal to or smaller than the number of carbon atoms of the cyclic structure $A^2$; and each wavy line independently represents a bond in the equatorial or axial conformation. Note that, from among the bonds of constituent atoms of the cyclic structure $A^2$, all bonds that neither form a ring nor bond with any of sulfur atom S, $R^1$ or $L^1$, are prescribed to have hydrogen atoms bound thereto.

The glycan in this invention is obtainable by subjecting the building block A and building block B of this invention, to glycosilation. Note that, for the convenience in this patent specification, the building block A is also referred to as "sugar donor" in the glycan synthesis, and the building block B is also referred to as "sugar acceptor" in the glycan synthesis. In this patent specification, the "glycan" is broadly understood in terms of the number of hydroxy groups. That is, in this patent specification, "glycan" not only means chain-like sugar compound having two or more hydroxy groups (—OH), but also means compound capable of yielding such chain-like compound after deblocked. Hence, the chain-like compound per se, directly obtainable by the production method of this invention, may be free of hydroxy group like a compound illustrated below. The chain-like compound free of hydroxy group is separately subjected to deblocking, to yield a chain-like sugar compound having two or more hydroxy groups (—OH). The deblocking reaction can be implemented by any of known methods, under conditions suitably determined depending on types of protective group.

[Chemical Formula 12]

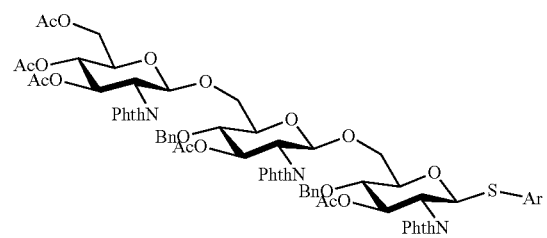

With a functional group having stronger electron attractiveness than before bound to the sulfur atom at the glycoside terminal, the present invention can improve the yield of streocontrolled glycan in oligosaccharide synthesis based on the liquid phase process, as compared with the prior method. The reason is estimated as follows.

In the oligosaccharide synthesis based on the liquid phase process with use of glycoside, an activated glycoside represented by Formula (S1) below (for example, glycosyl triflate in Reaction Formula (S1)) is recognized as an important reaction intermediate. For example, sugar donor 1t, when electrolytically oxidized at low temperatures in the presence of triflate anion $CF_3SO_3^-$, first yields glycosyl triflate as an intermediate of the glycosylation reaction, followed by accumulation. An active site (for example, triflate moiety) of the intermediate then reacts with a hydroxy group of a sugar acceptor 2t, thereby causing glycosylation between the sugar donor and the sugar acceptor to stereoselectively yield a glycan 3t. The reaction represented by Reaction Formula (S1) will also be referred to as main reaction, hereinafter.

Reaction Formula (S1)

[Chemical Formula 13]

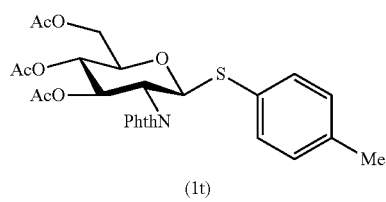

(1t)

Anodization

-continued

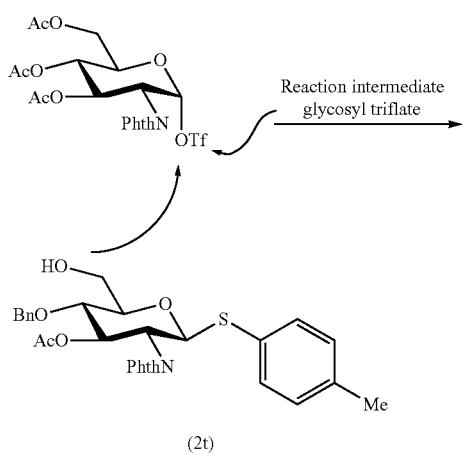

(2t)

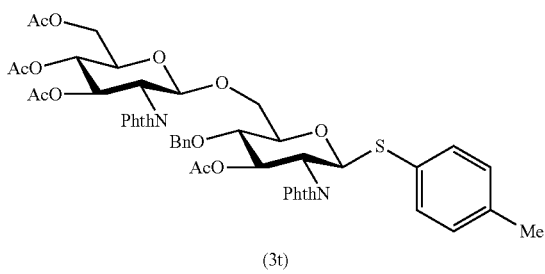

(3t)

The oligosaccharide syntheses by the known prior methods based on the liquid phase were, however, found in the present study to cause not a few side reactions other than the main reaction, consequently degrading efficiency of the main reaction. Such side reactions are estimated mainly as a sort of reaction represented by Reaction Formula (S2) below. More specifically, upon production of the reaction intermediate, the active site of the intermediate (for example, triflate moiety) reacts with the sulfur atom of the sugar acceptor 2t, whereby the reaction intermediate apparently returns back to the sugar donor 1t, presumably inhibiting glycosylation between the sugar donor it and the sugar acceptor 2t.

Reaction Formula (S2)

[Chemical Formula 14]

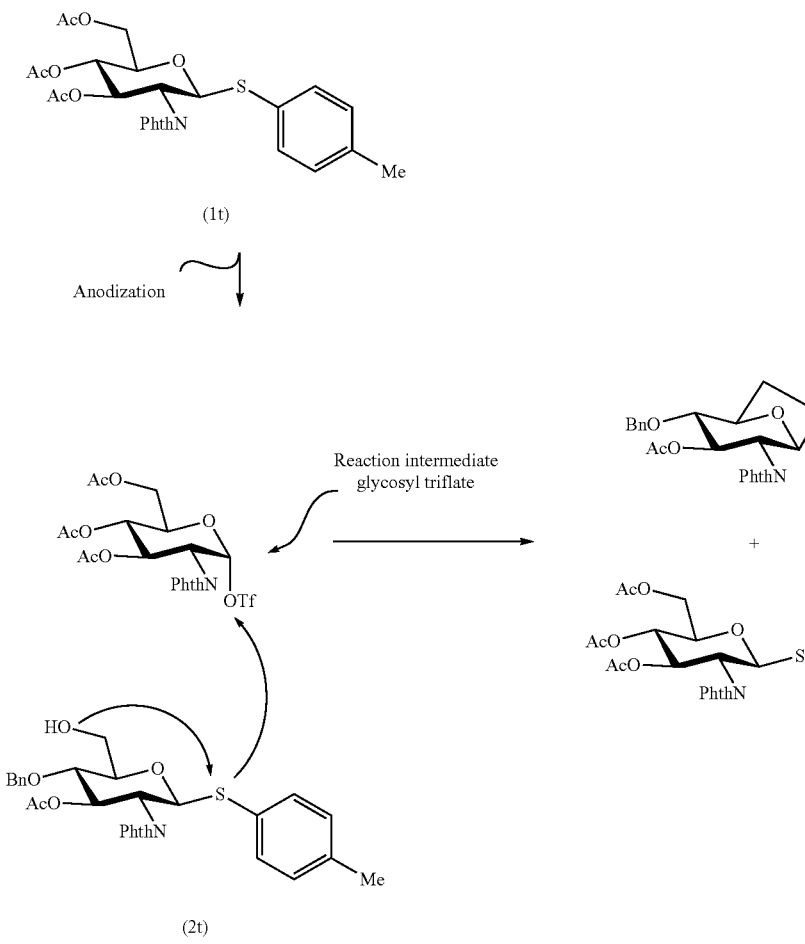

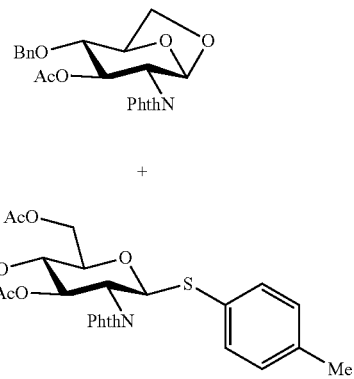

Now the building block of this invention has a functional group whose electron attractiveness is stronger than before, bound to the sulfur atom. This supposedly reduces, on a relative basis, electron density on the sulfur atom to reduce reactivity of the sulfur atom, and successfully suppresses the side reactions. This consequently improves the efficiency of the main reaction, and improves the yield ratio of glycan with high stereoselectivity (that is, the glycosidic bond is formed with a desired stereochemistry).

<<Building Block A>>

The building block A may be the building block solely by itself represented by Formula (1), or may be a building block that contains a sugar residue derived from the building block represented by Formula (1) and a sugar residue derived from the building block represented by Formula (2), or may be a mixture of them. Note that the building block represented by Formula (2) will be detailed collectively with the building block B.

In Formula (1), the cyclic structure $A^1$ is suitably designed depending on a structure of a target glycan to be produced, and is not specifically limited in relation to implementation of the production method of this invention. The number of carbon atoms in the cyclic structure $A^1$ is preferably 7 or smaller, and more preferably 6 or smaller. The number of oxygen atoms contained in the cyclic structure $A^1$ is usually one, although not specifically limited. In a case where the building block A is used for the glycan synthesis, the cyclic structure $A^1$ beneficially has only one oxygen atom in the cyclic structure. The cyclic structure $A^1$ preferably has a pyranose ring in which five carbon atoms and one oxygen atom occupy the vertices to form a six-membered ring, or, a furanose ring in which four carbon atoms and one oxygen atom occupy the vertices to form a five-membered ring. Note that the number of carbon atoms in the cyclic structure $A^1$ means the number of carbon atoms that compose the ring of the cyclic structure $A^1$.

The monovalent organic group represented by $R^1$ is not specifically limited, so long as the glycosylation reaction can proceed. The number of constituent atoms of the monovalent organic group is preferably 30 or smaller, from the viewpoint of forming the glycosidic bond at a specific desired site by the glycosylation reaction, which is more preferably 20 or smaller, and even more preferably 15 or smaller. By controlling the number of the constituent atoms to 30 or smaller, the glycosylation reaction with a neighboring building block will be less likely to be inhibited. Meanwhile, from the viewpoint of forming the glycosidic bond at a specified desired site, the number of constituent atoms is preferably 3 or larger, more preferably 4 or larger, and even more preferably 5 or larger. By controlling the number of the constituent atoms to 3 or larger, the bond form of the glycosidic bond will be more easily controlled to β-bond. Additionally from the viewpoint of forming the glycosidic bond at a desired specific site, $R^1$ is preferably bound to the C2 position neighboring the anomeric (C1) position.

$R^1$ preferably represents, for example, a phthalimido group, azido group, amido group, alkyl group, —[O(CH$_2$)$_i$]$_j$—OC$_k$H$_{2k+1}$ (where, i represents an integer from 1 to 10, j represents an integer from 0 to 5, k represents an integer from 1 to 10), —[O(CH$_2$)$_i$]$_j$—OC$_k$H$_{2k-1}$ (where, i represents an integer from 1 to 10, j represents an integer from 0 to 5, k represents an integer from 2 to 10), —O—C(=O)—C$_k$H$_{2k+1}$ (where, k represents an integer from 1 to 10), —O(CH$_2$)$_i$—Ar (where, i represents an integer from 1 to 10, Ar represents an aryl group having 6 to 10 carbon atoms), —O—C(=O)—Ar (where, Ar represents an aryl group having 6 to 10 carbon atoms) or alkylsiloxy group.

In a case where $R^1$ represents an amido group, the amido group may have, as a substituent, a straight-chain, branched or cyclic alkyl group, or aryl group. The number of carbon atoms of the alkyl group as the substituent is preferably 1 to 10, more preferably 1 to 6, and even more preferably 1 to 3. The number of carbon atoms of the aryl group as the substituent is preferably 6 to 10. The amido group, when having the substituent, specifically and preferably exemplified by methylamido group (acetylamino group), ethylamido group, n-propylamido group, isopropylamido group, n-butylamido group or t-butylamido group, or, phenylamido group (benzoylamino group) or naphthylamido group; more preferably acetylamino group, ethylamido group or benzoylamino group; and even more preferably acetylamino group or benzoylamino group.

The alkyl group may have a straight-chain, branched or cyclic structure, whose number of carbon atoms is preferably 1 to 10, more preferably 1 to 6, and even more preferably 1 to 3. The alkyl group is preferably, for example, methyl group, ethyl group, n-propyl group, isopropyl group, n-butyl group or t-butyl group; more preferably methyl group or ethyl group; and even more preferably methyl group.

The group —[O(CH$_2$)$_i$]$_j$—OC$_k$H$_{2k+1}$ (where, i represents an integer from 1 to 10, j represents an integer from 0 to 5, k represents an integer from 1 to 10) may have a straight-chain, branched or cyclic alkyl moiety C$_k$H$_{2k+1}$, and may have a straight-chain, branched or cyclic alkyl moiety (CH$_2$)$_i$. Each of the integers i and k in these alkyl moieties is preferably 1 to 6, more preferably 1 to 3, and even more preferably 1 or 2. The integer j is preferably 3 or smaller, more preferably 2 or smaller, even more preferably 1 or smaller, and may even be 0. That is, this group is particularly preferably —OC$_k$H$_{2k+1}$ (k represents an integer of 1 or 2) or —O(CH$_2$) i-OC$_k$H$_{2k+1}$ (i represents an integer of 1 or 2, k represents an integer of 1 or 2). More specifically, this group is preferably exemplified by methoxy group, ethoxy group, n-propyloxy group, —OCH$_2$OCH$_3$ (methoxymethyloxy group), —OC$_2$H$_4$OCH$_3$, —OCH$_2$OC$_2$H$_5$, —OC$_2$H$_4$OC$_2$H$_5$, —(OCH$_2$)$_2$OCH$_3$ or —(OCH$_2$)$_2$OC$_2$H$_5$; which is more preferably methoxy group, ethoxy group, n-propyloxy group, methoxymethyloxy group, —OC$_2$H$_4$OCH$_3$, —OCH$_2$OC$_2$H$_5$ or —OC$_2$H$_4$OC$_2$H$_5$; and even more preferably methoxy group or methoxymethyloxy group.

The group —O—[(CH$_2$)$_i$]$_j$—OC$_k$H$_{2k-1}$ (where, i represents an integer from 1 to 10, j represents an integer from 0 to 5, k represents an integer from 2 to 10) may have a straight-chain, branched or cyclic alkenyl moiety C$_k$H$_{2k-1}$, and may have a straight-chain, branched or cyclic alkyl moiety (CH$_2$)$_i$. The integer k in the alkenyl moiety is preferably 3 to 8, more preferably 3 to 6, and even more preferably 3 or 4. The integer i in the alkyl moiety is preferably 1 to 6, more preferably 1 to 3, and even more preferably 1 or 2. The integer j is preferably 3 or smaller, more preferably 2 or smaller, even more preferably 1 or smaller, and may even be 0. That is, the group is particularly preferably —OC$_3$H$_5$ or —O(CH$_2$)$_i$—OC$_3$H$_5$ (integer i represents 1 or 2). More specifically, the group is preferably, for example, an ethenyloxy group, 2-propenyloxy group, 3-butenyloxy group, —OCH$_2$OCH=CH$_2$, —OCH$_2$OCH$_2$CH=CH$_2$, —OCH$_2$OC$_2$H$_4$CH=CH$_2$, —OC$_2$H$_4$OCH=CH$_2$, —OC$_2$H$_4$OCH$_2$CH=CH$_2$ or —OC$_2$H$_4$OCH$_2$CH=CH$_2$; among which more preferred is 2-propenyloxy group, 3-butenyloxy group, —OCH$_2$OCH$_2$CH=CH$_2$ or —OCH$_2$OC$_2$H$_4$CH=CH$_2$; and even more preferred is 2-propenyloxy group or —OCH$_2$OCH$_2$CH=CH$_2$.

The group —O—C(=O)—$C_kH_{2k+1}$ (where, k represents an integer from 1 to 10) has a straight-chain, branched or cyclic alkyl moiety, wherein the integer k in the alkyl moiety is preferably from 1 to 6, more preferably from 1 to 3, and even more preferably 1 or 2. More specifically, the group is specifically a methylcarbonyloxy group (acetyloxy group), ethylcarbonyloxy group or n-propylcarbonyloxy group, and is more preferably an acetyloxy group.

The group —O($CH_2$)$_i$—Ar (where, i represents an integer from 1 to 10, Ar represents an aryl group having 6 to 10 carbon atoms) may have a phenyl group or naphthyl group, and preferably has a phenyl group. This group also has a straight-chain, branched or cyclic alkyl moiety $(CH_2)_i$. The integer i in the alkyl moiety is preferably 1 to 6, more preferably 1 to 3, and even more preferably 1 or 2. More specifically, this group is preferably, for example, —$OCH_2$-Ph (benzyloxy group), —$OC_2H_4$-Ph or —$OC_3H_6$-Ph, and more preferably benzyloxy group.

The group —O($CH_2$)$_i$—Ar also preferably has, in the aryl moiety thereof, an alkyl group having 1 to 10 carbon atoms or an alkyloxy group having 1 to 10 carbon atoms as a substituent. The number of carbon atoms of these substituents is preferably 1 to 6, more preferably 1 to 3, and even more preferably 1 or 2. More specifically, this substituent is preferably methyl group, ethyl group, methoxy group or ethoxy group, and more preferably methyl group or methoxy group. The number of substituents is preferably two or one, and more preferably one. Position of the substituent may be any of ortho (o-) position, meta (m-) position or para (p-) position, and is preferably para position. Hence, —O($CH_2$)$_i$—Ar when having the substituent is preferably o-, m- or p-methylbenzyloxy group or o-, m- or p-methoxybenzyloxy group, and is more preferably p-methylbenzyloxy group or p-methoxybenzyloxy group.

The group —O—C(=O)—Ar (where, Ar represents an aryl group having 6 to 10 carbon atoms) may have a phenyl group or naphthyl group, and preferably has a phenyl group. That is, this group is preferably a phenylcarbonyloxy group (benzoyloxy group).

The group —O—C(=O)—Ar also preferably has, in the aryl moiety thereof, an alkyl group having 1 to 10 carbon atoms or an alkyloxy group having 1 to 10 carbon atoms as a substituent. The number of carbon atoms of these substituents is preferably 1 to 6, more preferably 1 to 3, and even more preferably 1 or 2. More specifically, this substituent is preferably methyl group, ethyl group, methoxy group or ethoxy group, and more preferably methyl group or methoxy group. The number of substituents is preferably two or one, and more preferably one. Position of the substituent may be any of ortho (o-) position, meta (m-) position or para (p-) position, and is preferably para position. Hence, —O—C(=O)—Ar when having the substituent is preferably o-, m- or p-methylbenzoyloxy group, or o-, m- or p-methoxybenzoyloxy group, and is more preferably p-methylbenzoyloxy group or p-methoxybenzoyloxy group.

The alkylsiloxy group may be any of monoalkylsiloxy group, dialkylsiloxy group or trialkylsiloxy group, among which trialkylsiloxy group is preferred. The alkyl group in the alkylsiloxy group may have a straight-chain, branched or cyclic structure, among which the straight-chain structure is preferred. The number of carbon atoms of the alkyl group is preferably 1 to 6, more preferably 1 to 3, and even more preferably 1 or 2. More specifically, the alkylsiloxy group is preferably trimethylsiloxy group, dimethylsiloxy group, ethyldimethylsiloxy group, triethylsiloxy group, propyldimethylsiloxy group or t-butyldimethylsiloxy group, among which trimethylsiloxy group is more preferred.

In this invention, the organic group represented by $R^1$ may have a substituent other than those explained above. Such substituent is exemplified by halogen atom, cyano group, nitro group, hydrocarbon group, heterocyclic group, —$ORt^1$, —$CORt^1$, —$COORt^1$, —$OCORt^1$, —$NRt^1Rt^2$, —$NHCORt^1$, —$CONRt^1Rt^2$, —$NHCONRt^1Rt^2$, —$NHCO$-$ORt^1$, —$SRt^1$, —$SO_2Rt^1$, —$SO_2ORt^1$, —$NHSO_2Rt^1$ and —$SO_2NRt^1Rt^2$. Each of $Rt^1$ and $Rt^2$ independently represents a hydrogen atom, hydrocarbon group or heterocyclic group. $Rt^1$ and $Rt^2$, when given as hydrocarbon groups, may bind to each other to form a ring.

The halogen atom as the substituent is exemplified by fluorine atom, chlorine atom, bromine atom and iodine atom. The hydrocarbon group is exemplified by alkyl group, alkenyl group, alkynyl group and aryl group. The number of carbon atoms of the alkyl group is preferably 1 to 10, more preferably 1 to 5, and even more preferably 1 to 2. The alkyl group may have any of straight-chain, branched or cyclic structure, among which the straight-chain or branched structure is preferred, and the branched structure is more preferred. The number of carbon atoms of the alkenyl group is preferably 2 to 10, more preferably 2 to 5, and even more preferably 2 or 3. The alkenyl group may have any of straight-chain, branched and cyclic structures, among which the straight-chain or branched structure is preferred. The number of carbon atoms of the alkynyl group is preferably 2 to 10, and more preferably 2 to 5. The alkynyl group may have either straight-chain or branched structure, among which the straight-chain or branched structure is preferred. The number of carbon atoms of the aryl group is preferably 6 to 10, more preferably 6 to 8, and even more preferably 6 or 7. The heterocyclic group may be a monocycle, or may be a condensed ring. The heterocyclic group is preferably a monocycle or a condensed ring with the condensation number of 2 to 4. The number of heteroatoms that constitute the ring of the heterocyclic group is preferably 1 to 3. The heteroatom that constitutes the ring of the heterocyclic group is preferably nitrogen atom, oxygen atom or sulfur atom. The number of carbon atoms that constitutes the ring of the heterocyclic group is preferably 3 to 10, more preferably 3 to 8, and is even more preferably 3 to 5.

The hydrocarbon group and the heterocyclic group may further have a substituent, or may be unsubstituted. The substituent herein is exemplified by the aforementioned substituent.

$R^1$ is preferably free of substituent, from the viewpoint of formation of the glycosidic bond at a desired site and cost, whose particularly preferred examples include phthalimido group, azido group, acetyloxy group, acetamido group, benzyloxy group, p-methylbenzyloxy group, p-methoxybenzyloxy group, benzoyloxy group, p-methylbenzoyloxy group, p-methoxybenzoyloxy group, methyl group, ethyl group, methoxy group, ethoxy group, methoxymethyloxy group and trimethylsiloxy group; among which more preferred are phthalimido group, azido group, acetyloxy group, acetamido group, benzyloxy group and benzoyloxy group; and among which even more preferred are phthalimido group, azido group, acetyloxy group, acetamido group and benzyloxy group. From the viewpoint of forming the glycosidic bond at a desired site, m is preferably 1 to 3, more preferably 1 or 2, and even more preferably one. Each of m ($R^1$)s may independently represent the organic group. If m is 2 or larger, the ($R^1$)s may be the same organic group, or may be different organic groups.

$R^2$ is preferably a protective group for hydroxy group, and is not specifically limited if selected from those usually used as the protective group for hydroxy group of sugar compounds, since they are enough to protect the hydroxy group in the production method of this invention. $R^2$ is preferably, for example, a protective group for hydroxy group described in Protective Group in Organic Synthesis, Chapter 2, pp. 10-142, Theodora W. Greene and Peter G. M. Wuts, 2nd ed. More specifically, each $R^2$ independently and preferably represents, for example, alkyl group, —$(CH_2)_iO]_j$—$C_kH_{2k+1}$ (where, i represents an integer from 1 to 10, j represents an integer from 1 to 5, k represents an integer from 1 to 10), —C(=O)—$C_kH_{2k+1}$ (where, k represents an integer from 1 to 10), —$(CH_2)_i$—Ar (where, i represents an integer from 1 to 10, Ar represents an aryl group having 6 to 10 carbon atoms), or —C(=O)—Ar (where, Ar represents an aryl group having 6 to 10 carbon atoms).

The alkyl group may have any of straight-chain, branched or cyclic structure, and whose number of carbon atoms is preferably 1 to 10, more preferably 1 to 6, and even more preferably 1 to 3. The alkyl group is preferably, for example, methyl group, ethyl group, n-propyl group, isopropyl group, n-butyl group or t-butyl group, more preferably methyl group or ethyl group, and even more preferably methyl group.

The group —$[(CH_2)_iO]_j$—$C_kH_{2k+1}$ (where, i represents an integer from 1 to 10, j represents an integer from 0 to 5, k represents an integer from 1 to 10) may have a straight-chain, branched or cyclic alkyl moiety $C_kH_{2k+1}$, and may have a straight-chain, branched or cyclic alkyl moiety $(CH_2)_i$. Each of the integers i and k in these alkyl moieties is independently and preferably 1 to 6, more preferably 1 to 3, and even more preferably 1 or 2. The integer j is preferably 3 or smaller, more preferably 2 or smaller, even more preferably 1 or smaller, and even may be 0. That is, this group is particularly preferably —$C_kH_{2k+1}$ (k represents an integer of 1 or 2) or —$(CH_2)_i$—$OC_kH_{2k+1}$ (i represents an integer of 1 or 2, k represents an integer of 1 or 2). More specifically, this group is preferably, for example, methyl group, ethyl group, n-propyl group, —$CH_2OCH_3$ (methoxymethyl group: MOM), —$C_2H_4OCH_3$, —$CH_2OC_2H_5$, —$C_2H_4OC_2H_5$, —$(CH_2O)_2CH_3$ or —$(CH_2O)_2C_2H_5$; more preferably methyl group, ethyl group, n-propyl group, methoxymethyl group, —$C_2H_4OCH_3$, —$CH_2OC_2H_5$ or —$C_2H_4OC_2H_5$; and even more preferably methyl group or methoxymethyl group.

The group —C(=O)—$C_kH_{2k+1}$ (where, k represents an integer from 1 to 10) has a straight-chain, branched or cyclic alkyl moiety, integer k in the alkyl moiety preferably represents 1 to 6, more preferably represents 1 to 3, and even more preferably represents 1 or 2. More specifically, this group is preferably, for example, methylcarbonyl group (acetyl group), ethylcarbonyl group or n-propylcarbonyl group; and more preferably acetyl group.

The group —$(CH_2)_i$—Ar (where, i represents an integer from 1 to 10, Ar represents an aryl group having 6 to 10 carbon atoms) may have a phenyl group or naphthyl group, and preferably has a phenyl group. This group also has a straight-chain, branched or cyclic alkyl moiety $(CH_2)$. The integer i in the alkyl moiety is preferably 1 to 6, more preferably 1 to 3, and even more preferably 1 or 2. More specifically, the group is preferably, for example, —$CH_2$-Ph (benzyl group), —$C_2H_4$-Ph or —$C_3H_6$-Ph, among which benzyl group is preferred.

Moreover, —$(CH_2)_i$—Ar also preferably has an alkyl group having 1 to 10 carbon atoms or an alkyloxy group having 1 to 10 carbon atoms, as a substituent in the aryl moiety thereof. Details of preferred substituent are same as those of —$O(CH_2)_i$—Ar for $R^1$. Hence, —$(CH_2)_i$—Ar when having the substituent is preferably o-, m- or p-methylbenzyl group, or o-, m- or p-methoxybenzyl group; and is more preferably p-methylbenzyl group or p-methoxybenzyl group.

The group —C(=O)—Ar (where, Ar represents an aryl group having 6 to 10 carbon atoms) may have a phenyl group or a naphthyl group, and preferably has a phenyl group. That is, the group is preferably phenylcarbonyl group (benzoyl group).

Moreover, the —C(=O)—Ar also preferably has an alkyl group having 1 to 10 carbon atoms or an alkyloxy group having 1 to 10 carbon atoms, as a substituent in the aryl moiety thereof. Details of preferred substituent are same as those of —O—C(=O)—Ar for $R^1$. Hence, —C(=O)—Ar when having the substituent is preferably o-, m- or p-methylbenzoyl group, or o-, m- or p-methoxybenzoyl group; and is more preferably p-methylbenzoyl group or p-methoxybenzoyl group.

The alkylsilyl group may be any of monoalkylsilyl group, dialkylsilyl group or trialkylsilyl group, among which trialkylsilyl group is preferred. The alkyl group in the alkylsilyl group may have a straight-chain, branched or cyclic structure, among which the straight-chain structure is preferred. The number of carbon atoms of the alkyl group is preferably 1 to 6, more preferably 1 to 3, and even more preferably 1 or 2. More specifically, the alkylsilyl group is preferably, for example, trimethylsilyl group, dimethylsilyl group, ethyldimethylsilyl group, triethylsilyl group, propyldimethylsilyl group or t-butyldimethylsilyl group, among which trimethylsilyl group is preferred.

$R^2$ is preferably free of substituent, from the viewpoints of forming a glycosidic bond at a desired site, and cost, whose particularly preferred examples include methyl group, ethyl group, acetyl group, trimethylacetyl group, benzyl group, p-methylbenzyl group, p-methoxybenzyl group, benzoyl group, p-methylbenzoyl group, p-methoxybenzoyl group, trimethylsilyl group and t-butyldimethylsilyl group; among which more preferred are acetyl group, trimethylacetyl group, acetylamido group, benzyl group and benzoyl group.

In this invention, the organic group represented by $R^2$ may have a substituent other than those explained above, but is preferably free of substituent. Such substituent is exemplified by halogen atom, cyano group, nitro group, hydrocarbon group, heterocyclic group, —$ORt^1$, —$CORt^1$, —CO-$ORt^1$, —$OCORt^1$, —$NRt^1Rt^2$, —$NHCORt^1$, —$CONRt^1Rt^2$, —$NHCONRt^1Rt^2$, —$NHCOORt^1$, —$SRt^1$, —$SO_2Rt^1$, —$SO_2ORt^1$, —$NHSO_2Rt^1$ and —$SO_2NRt^1Rt^2$. Each of $Rt^1$ and $Rt^2$ independently represents a hydrogen atom, hydrocarbon group or heterocyclic group. $Rt^1$ and $Rt^2$, both when given as a hydrocarbon group, may bind to each other to form a ring. Other details are same as those of the substituents for $R^1$.

The divalent linking group represented by $L^1$ is preferably a group composed of one of, or combination of two or more groups selected from optionally substituted straight-chain or branched alkylene group, optionally substituted straight-chain or branched alkenylene group, —O—, —C(=O)—, —NR— and —S—. Now, R represents a hydrogen atom or a substituent. The substituent is as described above, and R is preferably a hydrogen atom. The number of carbon atoms of the optionally substituted alkylene group is preferably 1 to 5 and more preferably 1 to 3. The optionally substituted alkylene group is more preferably a methylene group or an ethylene group. The number of carbon atoms of the optionally substituted alkenylene group is preferably 2 to 5, and more preferably 2 or 3. The optionally substituted alkenylene group is more preferably vinyl group or propenyl group. In particular, $L^1$ is preferably a single bond, or an optionally substituted $C_{1-5}$ alkylene group, and more preferably single bond, methylene group or ethylene group.

The number n is suitably determined so far as m+n falls on or below the number of carbon atoms of the cyclic structure $A^1$. Choice of the number of n makes it possible to control the number of hydroxy groups in a glycan or deblocked glycan. The number n is preferably an integer from 2 to "the number of carbon atoms of cyclic structure $A^1$-2", and more preferably 2 or 3. Each of n ($R^2O-L^1$)s may independently represent the aforementioned organic group, and if n is 2 or larger, the ($R^2O-L^1$)s may be the same organic group, or may be different organic groups.

In this invention, a particularly preferred case is given by Formula (1) in which $A^1$ represents a pyranose ring or a furanose ring; each $R^1$ independently represents an unsubstituted, phthalimido group, azido group, acetyloxy group, acetamido group, benzyloxy group, p-methylbenzyloxy group, p-methoxybenzyloxy group, benzoyloxy group, p-methylbenzoyloxy group, p-methoxybenzoyloxy group, methyl group, ethyl group, methoxy group, ethoxy group, methoxymethyloxy group or trimethylsiloxy group; each $R^2$ independently represents an unsubstituted, methyl group, ethyl group, acetyl group, trimethylacetyl group, benzyl group, p-methylbenzyl group, p-methoxybenzyl group, benzoyl group, p-methylbenzoyl group, p-methoxybenzoyl group, trimethylsilyl group or t-butyldimethylsilyl group; and each $L^1$ independently represents a single bond or an unsubstituted methylene group or ethylene group. In a more preferred case given by Formula (1), $A^1$ represents a furanose ring, each $R^1$ independently represents an unsubstituted, phthalimido group, azido group, acetyloxy group, acetamido group, benzyloxy group or benzoyloxy group; each $R^2$ independently represents an unsubstituted, methyl group, acetyl group, benzyl group or benzoyl group, and each $L^1$ independently represents a single bond or an unsubstituted methylene group.

The building block represented by Formula (1) employed here is more preferably a building block represented by Formula (1-2) below.

Formula (1-2)

[Chemical Formula 15]

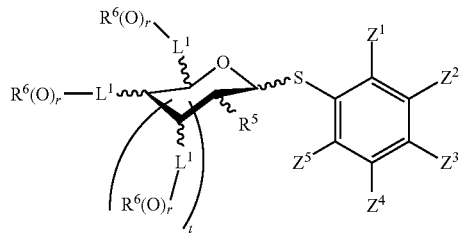

In Formula (1-2), each of $Z^1$ to $Z^5$ independently represents a hydrogen atom or an electron attractive group, with the total of the Hammett's σ values of $Z^1$ to $Z^5$ exceeding 0.12;

each $L^1$ independently represents a single bond or a divalent linking group;

each of $R^5$ and $R^6$ independently represents a monovalent organic group;

$R^5$ and $R^6$ may bind to each other to form a ring;

t represents an integer from 0 to 4;

each r independently represents 0 or 1; and each wavy line independently represents a bond in the equatorial or axial conformation.

$Z^1$ to $Z^5$, $R^5$, $R^6$ and $L^1$ in Formula (1-2) are synonymous to $Z^1$ to $Z^5$, $R^1$, $R^2$ and $L^1$ in Formula (1), respectively. In Formula (1-2), t=0 or 1 is preferred, which means that the cyclic structure $A^1$ is preferably a furanose ring or a pyranose ring. In addition, all (r)s individually represent 1. $L^1$ that is bound to the carbon atom at the C5 position next to oxygen atom preferably represents a methylene group, and other ($L^1$)s preferably represent a single bond.

The building block represented by Formula (1) or Formula (1-2) preferably has a molecular weight of 350 to 900, which is more preferably 400 to 800, even more preferably 450 to 750, and particularly preferably 500 to 700.

Preferred embodiment of the cyclic structure $A^1$ and the periphery thereof in Formula (1) are as follows.

[Chemical Formula 16]

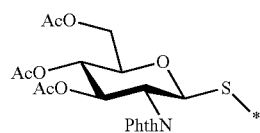
Sa-1

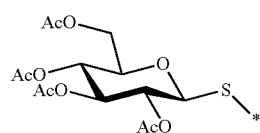
Sa-2

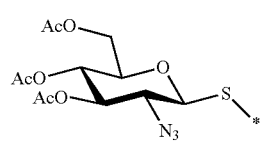
Sa-3

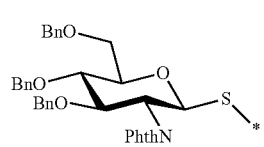
Sa-4

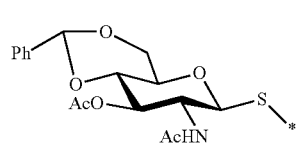
Sa-5

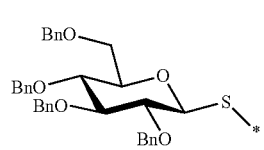
Sa-6

[Chemical Formula 17]

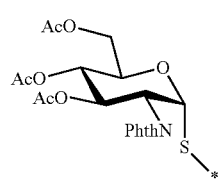
Sa-7

-continued

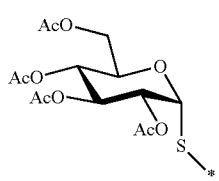

Sa-8

Sulfur atom S may bind to any site on the cyclic structure $A^1$, and preferably binds to the carbon atom next to oxygen atom (so-called anomeric position). The sulfur atom may be either in the equatorial or axial conformation with respect to the cyclic structure $A^1$, wherein the equatorial conformation is more preferred.

Types and the number of the electron attractive groups represented by $Z^1$ to $Z^5$ are not specifically limited, so long as the total of the individual Hammett's σ values exceeds 0.12. In this patent specification, "electron attractive group" means a substituent whose Hammett's substituent constant is positive at all of the ortho, meta and para positions of atom X, and the Hammett's "σ value" means the Hammett's substituent constant σ. The Hammett's substituent constant σ is determined on the basis of a dissociation reaction in aqueous solutions of benzoic acid and derivatives thereof at 25° C. Note that the Hammett's substituent constant given by a negative value means that the substituent is electron-donating.

The σ values at the meta position and para position have been known for a number of substituents as listed in *Chem. Rev.*, 1991, vol. 91, pp. 165-195. The a values listed in the literature will be directly recited in this specification. Meanwhile, any substituent whose a value is unknown may be calculated by the method described in the literature. The a values for the ortho position, which usually close to the values for the para position, will be represented by the a values for the para position.

The electron attractive group is preferably at least one of halogen atoms, nitro group, cyano group, azido group, halogenated alkyl group or acyl group; more preferably at least one of halogen atoms; and even more preferably at least either chlorine atom or bromine atom.

The σ values of representative substituents are listed in Table 1 below.

TABLE 1

| | Hammett's substituent constant σ | |
|---|---|---|
| | Meta position | Para position |
| F | 0.34 | 0.06 |
| Cl | 0.37 | 0.23 |
| Br | 0.39 | 0.23 |
| I | 0.35 | 0.18 |
| $NO_2$ | 0.71 | 0.78 |
| CN | 0.56 | 0.66 |
| $N_3$ | 0.37 | 0.08 |
| $CF_3$ | 0.43 | 0.54 |
| $CHF_2$ | 0.29 | 0.32 |
| $CH_2F$ | 0.12 | 0.11 |
| $CCl_3$ | 0.40 | 0.46 |
| $CHCl_2$ | 0.31 | 0.32 |
| $CH_2Cl$ | 0.11 | 0.12 |
| CHO | 0.35 | 0.42 |
| $CF_2CF_3$ | 0.47 | 0.52 |

TABLE 1-continued

| | Hammett's substituent constant σ | |
|---|---|---|
| | Meta position | Para position |
| COMe | 0.38 | 0.50 |
| H | 0.00 | 0.00 |
| Me | −0.07 | −0.17 |

The total of the Hammett's σ values of $Z^1$ to $Z^5$ is preferably 0.15 or larger, more preferably 0.2 or larger, and even more preferably 0.22 or larger. The larger the a value, the more largely electron density of the sulfur atom reduces, making it possible to suppress the reactivity. The total of the σ values is preferably 2 or smaller. With the total of the σ values controlled to 2 or smaller, the sugar donor will be more easily activated (allowed to produce the reaction intermediate). The total of the σ values is more preferably 1.5 or smaller, and even more preferably 1.0 or smaller.

Preferred combinations of $Z^1$ to $Z^5$ are as follows.

[Chemical Formula 18]

Sb-1

Total of σ values = 0.23

Sb-2

Total of σ values = 0.37

Sb-3

Total of σ values = 0.6

Sb-4

Total of σ values = 0.46

Sb-5

Total of σ values = 0.23

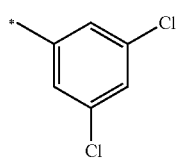

Total of σ values = 0.74

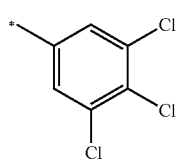

Total of σ values = 0.97

[Chemical Formula 19]

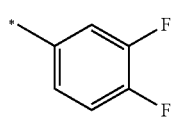

Total of σ values = 0.4

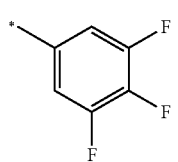

Total of σ values = 0.74

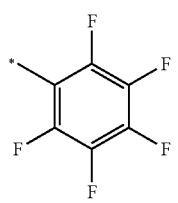

Total of σ values = 0.86

[Chemical Formula 20]

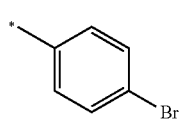

Total of σ values = 0.23

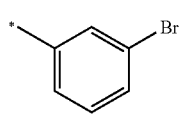

Total of σ values = 0.39

Sb-6

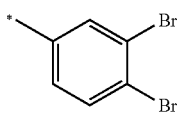

Total of σ values = 0.62

Sb-7

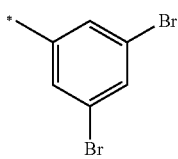

Total of σ values = 0.78

[Chemical Formula 21]

Sb-8

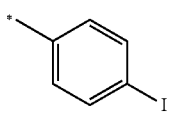

Total of σ values = 0.18

Sb-9

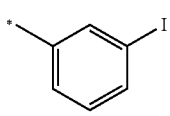

Total of σ values = 0.35

Sb-10

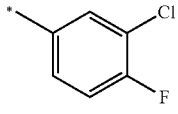

Total of σ values = 0.43

Sb-11

Total of σ values = 0.78

Sb-12

Sb-13

Sb-14

Sb-15

Sb-16

Sb-17

Sb-18

Preferred specific examples of the building block represented by Formula (1) are as follows. In the table, "Sa" represents a partial structure (containing sulfur atom) on the side of the cyclic structure $A^1$ in Formula (1), and "Sb" represents a partial structure (free of sulfur atom) on the side of the phenyl group in Formula (1). Symbols in the "Sa" column represent the individual symbols for the specific examples having been enumerated as the preferred embodiments of the cyclic structure $A^1$ and the periphery thereof, and symbols in the "Sb" column represents the individual symbols for the specific examples having been enumerated as the preferred combinations of $Z^1$ to $Z^5$. Each compound listed in the table has a partial structure listed in the "Sa" column, and a partial structure listed in the "Sb" column bound at a position indicated by asterisk "*"

[Chemical Formula 22]

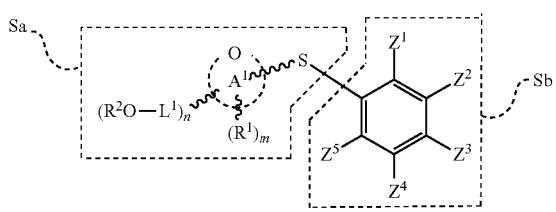

Formula (1)

TABLE 2

| Compound No. | Sa | Sb |
|---|---|---|
| Ca-1 | Sa-1 | Sb-1 |
| Ca-2 | Sa-2 | Sb-1 |
| Ca-3 | Sa-3 | Sb-1 |
| Ca-4 | Sa-4 | Sb-1 |
| Ca-5 | Sa-5 | Sb-1 |
| Ca-6 | Sa-6 | Sb-1 |
| Ca-7 | Sa-7 | Sb-1 |
| Ca-8 | Sa-8 | Sb-1 |
| Ca-9 | Sa-1 | Sb-2 |
| Ca-10 | Sa-2 | Sb-2 |
| Ca-11 | Sa 3 | Sb-2 |
| Ca-12 | Sa-4 | Sb-2 |
| Ca-13 | Sa-5 | Sb-2 |
| Ca-14 | Sa-6 | Sb-2 |
| Ca-15 | Sa-7 | Sb-2 |
| Ca-16 | Sa-8 | Sb-2 |
| Ca-17 | Sa-1 | Sb-6 |
| Ca-18 | Sa-2 | Sb-6 |
| Ca-19 | Sa-3 | Sb-6 |
| Ca-20 | Sa-4 | Sb 6 |
| Ca-21 | Sa-5 | Sb-6 |
| Ca-22 | Sa-6 | Sb-6 |
| Ca-23 | Sa-7 | Sb-6 |
| Ca-24 | Sa-8 | Sb-6 |
| Ca-25 | Sa-1 | Sb-7 |
| Ca-26 | Sa-2 | Sb-7 |
| Ca-27 | Sa-3 | Sb-7 |
| Ca-28 | Sa-4 | Sb-7 |
| Ca-29 | Sa-5 | Sb-7 |
| Ca-30 | Sa-6 | Sb-7 |
| Ca-31 | Sa-7 | Sb-7 |
| Ca-32 | Sa-8 | Sb-7 |
| Ca-33 | Sa-1 | Sb-9 |
| Ca-34 | Sa-2 | Sb-9 |
| Ca-35 | Sa-3 | Sb-9 |
| Ca-36 | Sa-4 | Sb-9 |
| Ca-37 | Sa-5 | Sb-9 |
| Ca-38 | Sa-6 | Sb-9 |
| Ca-39 | Sa-7 | Sb-9 |
| Ca-40 | Sa-8 | Sb-9 |
| Ca-41 | Sa-1 | Sb-11 |
| Ca-42 | Sa-2 | Sb-11 |
| Ca-43 | Sa-3 | Sb-11 |
| Ca-44 | Sa-4 | Sb-11 |
| Ca-45 | Sa-5 | Sb-11 |
| Ca-46 | Sa-6 | Sb-11 |
| Ca-47 | Sa-7 | Sb-11 |
| Ca-48 | Sa-8 | Sb-11 |
| Ca-49 | Sa-1 | Sb-3 |
| Ca-50 | Sa-2 | Sb-3 |
| Ca-51 | Sa-3 | Sb-3 |
| Ca-52 | Sa-4 | Sb-3 |
| Ca-53 | Sa-5 | Sb-3 |
| Ca-54 | Sa-6 | Sb-3 |
| Ca-55 | Sa-1 | Sb-8 |
| Ca-56 | Sa-2 | Sb-8 |
| Ca-57 | Sa-3 | Sb-8 |
| Ca-58 | Sa-4 | Sb-8 |
| Ca-59 | Sa-5 | Sb-8 |
| Ca-60 | Sa-6 | Sb-8 |
| Ca-61 | Sa-1 | Sb-12 |
| Ca-62 | Sa-2 | Sb-12 |
| Ca-63 | Sa-3 | Sb-12 |
| Ca-64 | Sa-4 | Sb-12 |
| Ca-65 | Sa-5 | Sb-12 |
| Ca-66 | Sa-6 | Sb-12 |
| Ca-67 | Sa-1 | Sb-13 |
| Ca-68 | Sa-2 | Sb-13 |
| Ca-69 | Sa-3 | Sb-13 |
| Ca-70 | Sa-4 | Sb-13 |
| Ca-71 | Sa-1 | Sb-14 |
| Ca-72 | Sa-2 | Sb-14 |
| Ca-73 | Sa-3 | Sb-14 |
| Ca-74 | Sa-4 | Sb-14 |
| Ca-75 | Sa-1 | Sb-15 |
| Ca-76 | Sa-2 | Sb-15 |
| Ca-77 | Sa-3 | Sb-15 |
| Ca-78 | Sa-4 | Sb-15 |
| Ca-79 | Sa-1 | Sb-17 |
| Ca-80 | Sa-5 | Sb-17 |

Possible embodiments of the building block A that contains a sugar residue derived from the building block represented by Formula (1) and a sugar residue derived from the building block represented by Formula (2) are as follows. This sort of building block A is obtainable, for example, by subjecting the building block represented by Formula (1) and the building block represented by Formula (2) to glycosylation. Such glycosylation if repeated multiple times also enables preparation of the building block A with a trisaccharide or tetrasaccharide structure. Bonds in the glycan may be either β-bond (bond that directs the sulfur atom in the equatorial conformation) or α-bond (bond that directs the sulfur atom in the axial conformation); and may be any of C1-C3 bond, C1-C4 bond, C1-C5 bond and C1-C6 bond.

[Chemical Formula 23]

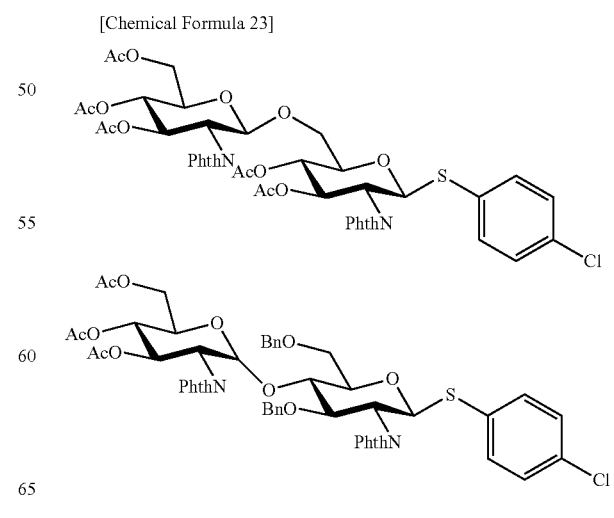

Preferred embodiments of the sugar residue derived from the building block represented by Formula (1) are as follows.

[Chemical Formula 24]

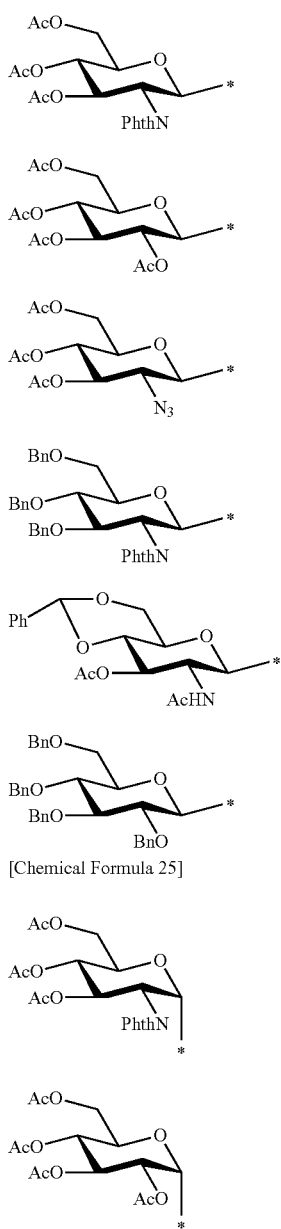

[Chemical Formula 25]

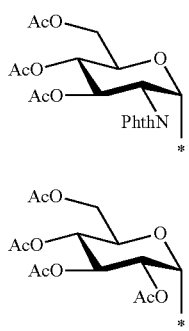

Preferred specific examples of the building block A that contains the sugar residue derived from the building block represented by Formula (1) and the sugar residue derived from the building block represented by Formula (2) are as follows. In the table, "Sf" represents the sugar residue derived from the building block represented by Formula (1), and "Sg" represents the sugar residue derived from the building block represented by Formula (2). Symbols in the "Sf" column represent the individual symbols for the specific examples having been enumerated as the preferred embodiments of the sugar residue derived from the building block represented by Formula (1), and symbols in the "Sg" column represent the individual symbols for the specific examples which will be separately explained below as the preferred embodiments of the sugar residue derived from the building block represented by Formula (2). Each compound listed in the table has a structure "Sf-Sg—S—Sb" in which a partial structure listed in the "Sf" column, a partial structure listed in the "Sg" column, a sulfur atom (*—S—*), and a partial structure listed in the "Sb" column are bound in sequence at the positions indicated by asterisks "*". Note that the sulfur atom shall be interposed, as described above, between the partial structure listed in the "Sg" column and the partial structure listed in the "Sb" column.

TABLE 3

| CompoundNo. | Sf | Sg | Sb |
|---|---|---|---|
| Cc-1 | Sf-1 | Sg-1 | Sb-1 |
| Cc-2 | Sf-1 | Sg-2 | Sb-1 |
| Cc-3 | Sf-1 | Sg-3 | Sb-11 |
| Cc-4 | Sf-1 | Sg-4 | Sb-11 |
| Cc-5 | Sf-1 | Sg-5 | Sb-6 |
| Cc-6 | Sf-1 | Sg-6 | Sb-6 |
| Cc-7 | Sf-1 | Sg-7 | Sb-7 |
| Cc-8 | Sf-1 | Sg-8 | Sb-7 |
| Cc-9 | Sf-1 | Sg-9 | Sb-9 |
| Cc-10 | Sf-1 | Sg-10 | Sb-12 |
| Cc-11 | Sf-1 | Sg-11 | Sb-14 |
| Cc-12 | Sf-2 | Sg-1 | Sb-1 |
| Cc-13 | Sf-2 | Sg-2 | Sb-1 |
| Cc-14 | Sf-2 | Sg-3 | Sb-11 |
| Cc-15 | Sf-2 | Sg-4 | Sb-11 |
| Cc-16 | Sf-2 | Sg-5 | Sb-6 |
| Cc-17 | Sf-2 | Sg-6 | Sb-6 |
| Cc-18 | Sf-2 | Sg-7 | Sb-7 |
| Cc-19 | Sf-2 | Sg-8 | Sb-8 |
| Cc-20 | Sf-2 | Sg-9 | Sb-9 |
| Cc-21 | Sf-2 | Sg-10 | Sb-12 |
| Cc-22 | Sf-2 | Sg-11 | Sb-15 |
| Cc-23 | Sf-3 | Sg-1 | Sb-11 |
| Cc-24 | Sf-3 | Sg-2 | Sb-11 |
| Cc-25 | Sf-3 | Sg-3 | Sb-18 |
| Cc-26 | Sf-3 | Sg-4 | Sb-1 |
| Cc-27 | Sf-3 | Sg-5 | Sb-7 |
| Cc-28 | Sf-3 | Sg-6 | Sb-7 |
| Cc-29 | Sf-3 | Sg-7 | Sb-6 |
| Cc-30 | Sf-3 | Sg-8 | Sb-6 |
| Cc-31 | Sf-3 | Sg-9 | Sb-12 |
| Cc-32 | Sf-3 | Sg-10 | Sb-14 |
| Cc-33 | Sf-3 | Sg-11 | Sb-17 |
| Cc-34 | Sf-4 | Sg-1 | Sb-18 |
| Cc-35 | Sf-4 | Sg-2 | Sb-15 |
| Cc-36 | Sf-4 | Sg-3 | Sb-7 |
| Cc-37 | Sf-4 | Sg-4 | Sb-7 |
| Cc-38 | Sf-4 | Sg-5 | Sb-6 |
| Cc-39 | Sf-4 | Sg-6 | Sb-1 |
| Cc-40 | Sf-4 | Sg-7 | Sb-1 |
| Cc-41 | Sf-4 | Sg-8 | Sb-11 |
| Cc-42 | Sf-4 | Sg-9 | Sb-11 |
| Cc-43 | Sf-4 | Sg-10 | Sb-2 |
| Cc-44 | Sf-4 | Sg-11 | Sb-3 |
| Cc-45 | Sf-5 | Sg-1 | Sb-1 |
| Cc-46 | Sf-5 | Sg-2 | Sb-1 |
| Cc-47 | Sf-5 | Sg-3 | Sb-11 |
| Cc-48 | Sf-5 | Sg-4 | Sb-11 |
| Cc-49 | Sf-5 | Sg-5 | Sb-6 |
| Cc-50 | Sf-5 | Sg-6 | Sb-6 |
| Cc-51 | Sf-5 | Sg-7 | Sb-7 |
| Cc-52 | Sf-5 | Sg-8 | Sb-7 |
| Cc-53 | Sf-5 | Sg-9 | Sb-9 |
| Cc-54 | Sf-5 | Sg-10 | Sb-12 |
| Cc-55 | Sf-5 | Sg-11 | Sb-14 |
| Cc-56 | Sf-6 | Sg-1 | Sb-1 |
| Cc-57 | Sf-6 | Sg-2 | Sb-1 |
| Cc-58 | Sf-6 | Sg-3 | Sb-11 |
| Cc-59 | Sf-6 | Sg-4 | Sb-11 |
| Cc-60 | Sf-6 | Sg-5 | Sb-6 |
| Cc-61 | Sf-6 | Sg-6 | Sb-6 |
| Cc-62 | Sf-6 | Sg-7 | Sb-7 |

TABLE 3-continued

| CompoundNo. | Sf | Sg | Sb |
|---|---|---|---|
| Cc-63 | Sf-6 | Sg-8 | Sb-8 |
| Cc-64 | Sf-6 | Sg-9 | Sb-9 |
| Cc-65 | Sf-6 | Sg-10 | Sb-12 |
| Cc-66 | Sf-6 | Sg-11 | Sb-15 |
| Cc-67 | Sf-7 | Sg-1 | Sb-11 |
| Cc-68 | Sf-7 | Sg-2 | Sb-11 |
| Cc-69 | Sf-7 | Sg-3 | Sb-18 |
| Cc-70 | Sf-7 | Sg-4 | Sb-1 |
| Cc-71 | Sf-7 | Sg-5 | Sb-7 |
| Cc-72 | Sf-7 | Sg-6 | Sb-7 |
| Cc-73 | Sf-7 | Sg-7 | Sb-6 |
| Cc-74 | Sf-7 | Sg-8 | Sb-6 |
| Cc-75 | Sf-7 | Sg-9 | Sb-12 |
| Cc-76 | Sf-7 | Sg-10 | Sb-14 |
| Cc-77 | Sf-7 | Sg-11 | Sb-17 |
| Cc-78 | Sf-8 | Sg-1 | Sb-18 |
| Cc-79 | Sf-8 | Sg-2 | Sb-15 |
| Cc-80 | Sf-8 | Sg-3 | Sb-7 |
| Cc-81 | Sf-8 | Sg-4 | Sb-7 |
| Cc-82 | Sf-8 | Sg-5 | Sb-6 |
| Cc-83 | Sf-8 | Sg-6 | Sb-1 |
| Cc-84 | Sf-8 | Sg-7 | Sb-1 |
| Cc-85 | Sf-8 | Sg-8 | Sb-11 |
| Cc-86 | Sf-8 | Sg-9 | Sb-11 |
| Cc-87 | Sf-8 | Sg-10 | Sb-2 |
| Cc-88 | Sf-8 | Sg-11 | Sb-3 |

<<Building Block B>>

The building block B may be the building block solely by itself represented by Formula (2), or may be a building block that contains a plurality of sugar residues derived from the building block represented by Formula (2), or may be a mixture of them.

In Formula (2), the cyclic structure $A^2$ is suitably designed depending on a structure of a target glycan to be produced, and is not specifically limited in relation to implementation of the production method of this invention. The number of carbon atoms in the cyclic structure $A^2$ is preferably 7 or smaller, and more preferably 6 or smaller. In the cyclic structure $A^2$, also the number of oxygen atoms contained in the cyclic structure is not specifically limited, similarly to the building block represented by Formula (1). Only one oxygen atom is preferably contained at the vertex. In consideration of applications, the cyclic structure $A^2$ beneficially contains only one oxygen atom in the cyclic structure, and preferably has a pyranose ring in which five carbon atoms and one oxygen atom occupy the vertices to form a six-membered ring, or a furanose ring in which four carbon atoms and one oxygen atom occupy the vertices to form a five-membered ring.

The monovalent organic group represented by $R^3$ is not specifically limited, so long as the glycosylation reaction can proceed, similarly to $R^1$ in Formula (1). The number of constituent atoms of the monovalent organic group is preferably 30 or smaller, from the viewpoint of forming the glycosidic bond at a specific desired site by the glycosylation reaction, which is more preferably 20 or smaller, and even more preferably 15 or smaller. By controlling the number of the constituent atoms to 30 or smaller, the glycosylation reaction with a neighboring building block will be less likely to be inhibited. Meanwhile, from the viewpoint of forming the glycosidic bond at a specified desired site, the number of constituent atoms is preferably 3 or larger, more preferably 4 or larger, and even more preferably 5 or larger. By controlling the number of the constituent atoms to 3 or larger, the bond form of the glycosidic bond will be more easily controlled to β-bond.

$R^3$ preferably represents, for example, phthalimido group, azido group, $(C_{1-10}$ alkyloxy$)_n$ group (n represents an integer from 1 to 5), $C_{1-10}$ alkyl carbonyl group, $C_{1-10}$ alkyl carbonyloxy group, $C_{1-10}$ alkyl amido group or tri ($C_{1-5}$ alkylsiloxy) group, similarly to $R^1$ in Formula (1). Each of these organic groups may have a substituent, whose specific embodiments are same as those for $R^1$ in Formula (1). $R^3$ is preferably unsubstituted from the viewpoint of forming a glycosidic bond at a desired site; and especially, preferred is unsubstituted phthalimido group, azido group, acetyloxy group, acetamido group, benzyloxy group, benzoyloxy group, methoxy group, ethoxy group, methoxymethyloxy group or trimethylsiloxy group; more preferred is unsubstituted phthalimido group, azido group, acetyloxy group, acetamido group, benzyloxy group or benzoyloxy group; and even more preferred is unsubstituted phthalimido group, azido group, acetyloxy group, acetamido group or benzyloxy group. From the viewpoint of forming a glycosidic bond at a desired site, p preferably represents 1 to 3, more preferably represents 1 or 2, and even more preferably one. Each of p ($R^3$)s may independently represent the aforementioned organic group. When p is 2 or larger, ($R^3$)s may represent the same organic group, or different organic groups.

$R^4$, when representing the monovalent organic group, is preferably a protective group for hydroxy group, and is not specifically limited if selected from those usually used as the protective group for hydroxy group of sugar compounds. The protective group for hydroxy group is same as those represented by $R^2$ in Formula (1). The number of hydrogen atom in $R^4$ is preferably 3 or smaller, from the viewpoint of forming a glycosidic bond at a desired site, more preferably 2 or smaller, and even more preferably one. $R^4$ is preferably unsubstituted, from the viewpoint of forming a glycosidic bond at a desired site, whose particularly preferred examples include methyl group, ethyl group, acetyl group, trimethylacetyl group, benzyl group (for example, p-methoxybenzyl group, p-methylbenzyl group), benzoyl group, trimethylsilyl group and t-butyldimethylsilyl group; and more preferred examples include acetyl group, trimethylacetyl group, acetylamido group, benzyl group and benzoyl group.

The divalent linking group represented by $L^2$ is preferably a group composed of one of, or combination of two or more groups selected from optionally substituted $C_{1-5}$ alkylene group, —O—, —C(=O)—, —NR— and —S—. The number of carbon atoms of the optionally substituted alkylene group is preferably 1 to 3. The optionally substituted alkylene group is more preferably methylene group or ethylene group. Now R represents a substituent. The substituent is as descried above. In particular, $L^2$ preferably represents a single bond, or, optionally substituted $C_{1-5}$ alkylene group, and more preferably represents a single bond, methylene group or ethylene group.

The value q is suitably determined so far as p+q falls or below the number of carbon atoms of the cyclic structure $A^2$. The number of hydroxy groups in the glycan or deblocked glycan may be controlled on the basis of q. The value q is preferably an integer from 2 to "the number of carbon atoms in cyclic structure $A^2$-2", and more preferably 2 or 3. Each of q ($R^4O-L^2$)s may independently represent the aforementioned organic group, and if q is 2 or larger, the organic groups may be same as or different.

For the building block represented by Formula (2), a building block represented by Formula (2-2) below is further preferably used.

[Chemical Formula 26]

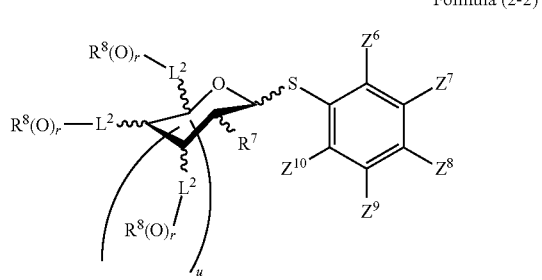

Formula (2-2)

In Formula (2-2), $Z^6$ to $Z^{10}$ independently represents a hydrogen atom or an electron attractive group, with the total of the Hammett's σ values of $Z^6$ to $Z^{10}$ exceeding 0.12, $R^7$ represents a monovalent organic group, each $R^8$ independently represents a hydrogen atom or a monovalent organic group, $R^7$ and $R^8$ may bind to each other to form a ring, u represents an integer from 0 to 4, each r independently represents 0 or 1, at least one of $(R^8(O)_r)$s represents a hydroxy group, and each wavy line independently represents a bond in the equatorial or axial conformation.

$Z^6$ to $Z^{10}$, $R^7$, $R^8$ and $L^2$ in Formula (2-2) are respectively same as $Z^6$ to $Z^{10}$, $R^3$, $R^4$ and $L^2$ in Formula (2). In Formula (2-2), u is preferably 0 or 1, that is, the cyclic structure $A^1$ preferably represents a furanose ring or pyranose ring. All of r preferably represent one.

The building block represented by Formula (2) or Formula (2-2) preferably has a molecular weight of 200 to 600, which is more preferably 250 to 550, and even more preferably 300 to 500.

Preferred embodiments of the cyclic structure $A^2$ and the periphery thereof represented by Formula (2) are typically as follows.

[Chemical Formula 27]

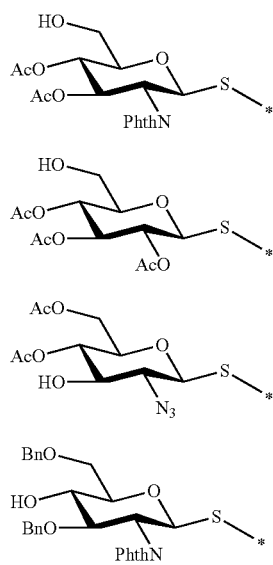

Sc-1

Sc-2

Sc-3

Sc-4

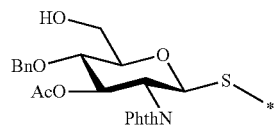

Sc-5

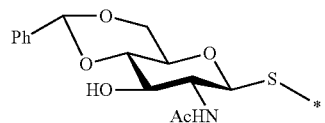

Sc-6

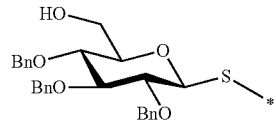

Sc-7

[Chemical Formula 28]

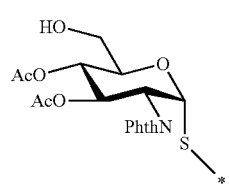

Sc-8

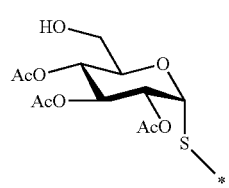

Sc-9

The sulfur atom may bind to any site on the cyclic structure $A^2$, and preferably binds to the carbon atom next to oxygen atom (so-called anomeric position). The sulfur atom may be either in the equatorial or axial conformation with respect to the cyclic structure $A^2$, wherein the equatorial conformation is more preferred.

Types and the number of the electron attractive groups represented by $Z^6$ to $Z^{10}$ are not specifically limited, so long as the total of the individual Hammett's σ values exceeds 0.12. The total of the Hammett's σ values is calculated similarly to the case of $Z^1$ to $Z^5$ in Formula (1). Combinations of $Z^1$ to $Z^5$ in Formula (1) may be same as, or different from combinations of $Z^6$ to $Z^{10}$ in Formula (2).

The total of the Hammett's σ values for $Z^6$ to $Z^{10}$ is preferably 0.15 or larger, more preferably 0.2 or larger, and even more preferably 0.22 or larger. The larger the total of the σ values, the more largely the electron density of the sulfur atom decreases, so that the reactivity can be reduced. The total of the σ values is preferably 2 or smaller. With the total of the σ values controlled to 2 or smaller, the sugar donor will be more easily activated (to produce the reaction intermediate) in the process of electrolytic oxidation. The total of the σ values is more preferably 1.5 or smaller, and even more preferably 1.0 or smaller. The total of the σ values for $Z^1$ to $Z^5$ in Formula (1) may be same as, or different from the total of the σ values for $Z^6$ to $Z^{10}$ in Formula (2).

Preferred combinations of $Z^6$ to $Z^{10}$ are same as those typically exemplified for $Z^1$ to $Z^5$. In particular, at least one of $Z^1$ to $Z^{10}$ preferably represents a halogen atom. Moreover it is preferred that at least one of $Z^1$ to $Z^5$ represents a halogen atom, and at least one of $Z^6$ to $Z^{10}$ represents a halogen atom. For example, a possible embodiment may be such that two of $Z^1$ to $Z^5$ represent halogen atoms and the other represent hydrogen atoms, and two of $Z^6$ to $Z^{10}$ represent halogen atoms and the other represent hydrogen atoms; or, such that one of $Z^1$ to $Z^5$ represents a halogen atom and the other represent hydrogen atoms, and one of $Z^6$ to $Z^{10}$ represents a halogen atom and the other represent hydrogen atoms.

Preferred specific examples of the building block represented by Formula (2) are as follows. In the table, "Sc" represents a partial structure (containing sulfur atom) on the side of the cyclic structure $A^2$ in Formula (2). Meanwhile, symbols in the "Sc" column represent the specific examples having been enumerated as the preferred embodiments of the cyclic structure $A^2$ and the periphery thereof. "Sb" represents a partial structure (excluding sulfur atom) on the side of the phenyl group, similarly to the case in Formula (1). Each compound listed in the table has a partial structure listed in the "Sc" column, and a partial structure listed in the "Sb" column bound at a position indicated by asterisk "*"

[Chemical Formula 29]

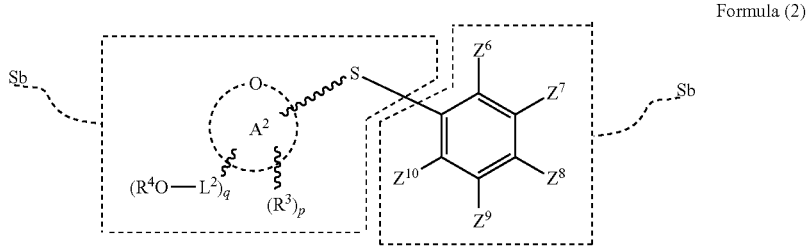

Formula (2)

TABLE 4

| Compound No. | Sc | Sb |
| --- | --- | --- |
| Cb-1 | Sc-1 | Sb-1 |
| Cb-2 | Sc-2 | Sb-1 |
| Cb-3 | Sc-3 | Sb-1 |
| Cb-4 | Sc-4 | Sb-1 |
| Cb-5 | Sc-5 | Sb-1 |
| Cb-6 | Sc-6 | Sb-1 |
| Cb-7 | Sc-7 | Sb-1 |
| Cb-8 | Sc-8 | Sb-1 |
| Cb-9 | Sc-1 | Sb-2 |
| Cb-10 | Sc-2 | Sb-2 |
| Cb-11 | Sc-3 | Sb-2 |
| Cb-12 | Sc-4 | Sb-2 |
| Cb-13 | Sc-5 | Sb-2 |
| Cb-14 | Sc-6 | Sb-2 |
| Cb-15 | Sc-7 | Sb-2 |
| Cb-16 | Sc-8 | Sb-2 |
| Cb-17 | Sc-1 | Sb-6 |
| Cb-18 | Sc-2 | Sb-6 |
| Cb-19 | Sc-3 | Sb-6 |
| Cb-20 | Sc-4 | Sb-6 |
| Cb-21 | Sc-5 | Sb-6 |
| Cb-22 | Sc-6 | Sb-6 |
| Cb-23 | Sc-7 | Sb-6 |
| Cb-24 | Sc-8 | Sb-6 |
| Cb-25 | Sc-1 | Sb-7 |
| Cb-26 | Sc-2 | Sb-7 |
| Cb-27 | Sc-3 | Sb-7 |
| Cb-28 | Sc-4 | Sb-7 |
| Cb-29 | Sc-5 | Sb-7 |
| Cb-30 | Sc-6 | Sb-7 |
| Cb-31 | Sc-7 | Sb-7 |
| Cb-32 | Sc-8 | Sb-7 |
| Cb-33 | Sc-1 | Sb-9 |
| Cb-34 | Sc-2 | Sb-9 |

TABLE 4-continued

| Compound No. | Sc | Sb |
| --- | --- | --- |
| Cb-35 | Sc-3 | Sb-9 |
| Cb-36 | Sc-4 | Sb-9 |
| Cb-37 | Sc-5 | Sb-9 |
| Cb-38 | Sc-6 | Sb-9 |
| Cb-39 | Sc-7 | Sb-9 |
| Cb-40 | Sc-8 | Sb-9 |
| Cb-41 | Sc-1 | Sb-11 |
| Cb-42 | Sc-2 | Sb-11 |
| Cb-43 | Sc-3 | Sb-11 |
| Cb-44 | Sc-4 | Sb-11 |
| Cb-45 | Sc-5 | Sb-11 |
| Cb-46 | Sc-6 | Sb-11 |
| Cb-47 | Sc-7 | Sb-11 |
| Cb-48 | Sc-8 | Sb-11 |
| Cb-49 | Sc-1 | Sb-3 |
| Cb-50 | Sc-2 | Sb-3 |
| Cb-51 | Sc-3 | Sb-3 |
| Cb-52 | Sc-4 | Sb-3 |
| Cb-53 | Sc-5 | Sb-3 |

TABLE 4-continued

| Compound No. | Sc | Sb |
| --- | --- | --- |
| Cb-54 | Sc-6 | Sb-3 |
| Cb-55 | Sc-1 | Sb-8 |
| Cb-56 | Sc-2 | Sb-8 |
| Cb-57 | Sc-3 | Sb-8 |
| Cb-58 | Sc-4 | Sb-8 |
| Cb-59 | Sc-5 | Sb-8 |
| Cb-60 | Sc-6 | Sb-8 |
| Cb-61 | Sc-1 | Sb-12 |
| Cb-62 | Sc-2 | Sb-12 |
| Cb-63 | Sc-3 | Sb-12 |
| Cb-64 | Sc-4 | Sb-12 |
| Cb-65 | Sc-5 | Sb-12 |
| Cb-66 | Sc-6 | Sb-12 |
| Cb-67 | Sc-1 | Sb-13 |
| Cb-68 | Sc-2 | Sb-13 |
| Cb-69 | Sc-3 | Sb-13 |
| Cb-70 | Sc-4 | Sb-13 |
| Cb-71 | Sc-1 | Sb-14 |
| Cb-72 | Sc-2 | Sb-14 |
| Cb-73 | Sc-3 | Sb-14 |
| Cb-74 | Sc-4 | Sb-14 |
| Cb-75 | Sc-1 | Sb-15 |
| Cb-76 | Sc-2 | Sb-15 |
| Cb-77 | Sc-3 | Sb-15 |
| Cb-78 | Sc-4 | Sb-15 |
| Cb-79 | Sc-1 | Sb-17 |
| Cb-80 | Sc-5 | Sb-17 |

A possible embodiment of the building block B, when composed of a building block that contains a plurality of sugar residues derived from the building block represented by Formula (2), is typically as follows. Such building block B is obtainable, for example, by subjecting the building blocks represented by Formula (2) to glycosylation. Such glycosilation if repeated multiple times also enables preparation of the building block B with a trisaccharide or tetrasaccharide structure. Alternatively, such building block B may be prepared by partially deblocking the glycan having been produced as the building block A. Bonds in the glycan may be either β-bond or α-bond; and may be any of C1-C3 bond, C1-C4 bond, C1-C5 bond and C1-C6 bond.

[Chemical Formula 30]

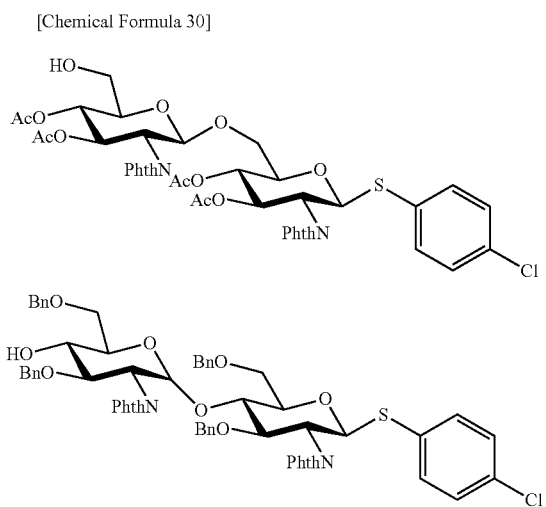

Preferred embodiments of the sugar residue derived from the building block represented by Formula (2) are typically as follows.

[Chemical Formula 31]

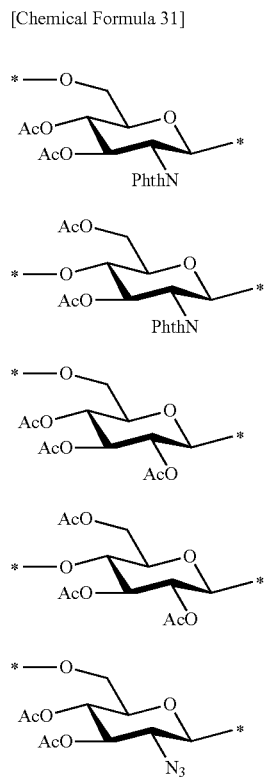

[Chemical Formula 32]

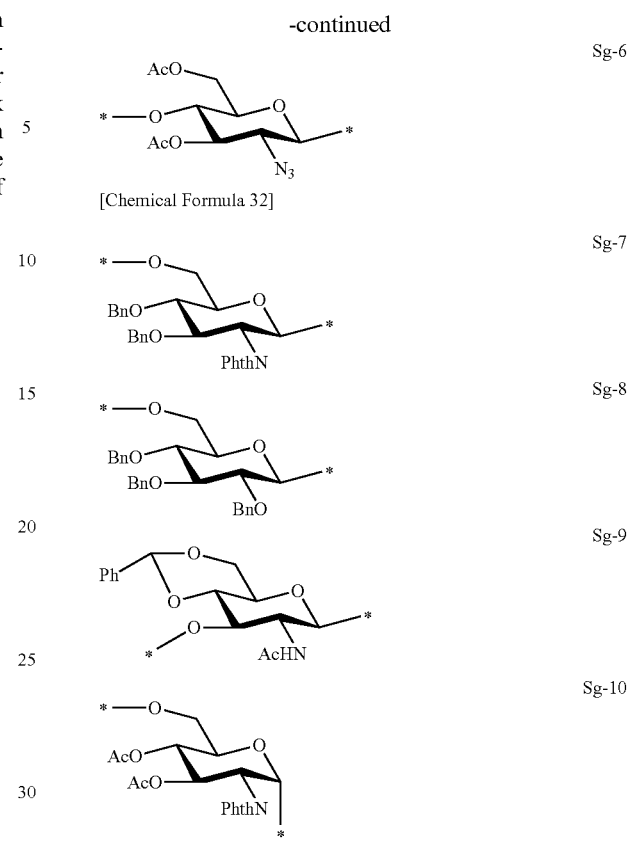

Preferred specific examples of the building block B that contains a plurality of the sugar residues derived from the building block represented by Formula (2) are as follows. In the table, "$Sg^1$" represents the first sugar residue derived from the building block represented by Formula (2), and "$Sg^2$" represents the second sugar residue derived from the building block represented by Formula (2). Symbols in the "$Sg^1$" and "$Sg^2$" columns represent specific examples having been enumerated as the preferred embodiments of the sugar residues derived from the building block represented by Formula (2). Each compound listed in the table has a structure "$Sg^1$—$Sg^2$—S—Sb" in which a partial structure listed in the "$Sg^1$" column, a partial structure listed in the "$Sg^2$" column, a sulfur atom (*—S—*), and a partial structure listed in the "Sb" column are bound in sequence at the positions indicated by asterisks "*". Note that, in the partial structures listed in the "$Sg^1$" column, any asterisk not involved in bond shall be replaced with a hydrogen atom, and a sulfur atom shall be interposed between the partial structure listed in the "$Sg^2$" column and the partial structure listed in the "Sb" structure, as described previously.

TABLE 5

| CompoundNo | Sg¹ | Sg² | Sb |
|---|---|---|---|
| Cd-1 | Sg-1 | Sg-1 | Sb-1 |
| Cd-2 | Sg-1 | Sg-2 | Sb-1 |
| Cd-3 | Sg-1 | Sg-3 | Sb-11 |
| Cd-4 | Sg-1 | Sg-4 | Sb-11 |
| Cd-5 | Sg-1 | Sg-5 | Sb-6 |
| Cd-6 | Sg-1 | Sg-6 | Sb-6 |
| Cd-7 | Sg-1 | Sg-7 | Sb-7 |
| Cd-6 | Sg-1 | Sg-8 | Sb-7 |
| Cd-9 | Sg-1 | Sg-9 | Sb-9 |
| Cd-10 | Sg-1 | Sg-10 | Sb-12 |
| Cd-11 | Sg-1 | Sg-11 | Sb-14 |
| Cd-12 | Sg-2 | Sg-1 | Sb-1 |
| Cd-13 | Sg-2 | Sg-2 | Sb-1 |
| Cd-14 | Sg-2 | Sg-3 | Sb-11 |
| Cd-15 | Sg-2 | Sg-4 | Sb-11 |
| Cd-16 | Sg-2 | Sg-5 | Sb-6 |
| Cd-17 | Sg-2 | Sg-6 | Sb-6 |
| Cd-18 | Sg-2 | Sg-7 | Sb-7 |
| Cd-19 | Sg-2 | Sg-8 | Sb-8 |
| Cd-20 | Sg-2 | Sg-9 | Sb-9 |
| Cd-21 | Sg-2 | Sg-10 | Sb-12 |
| Cd-22 | Sg-2 | Sg-11 | Sb-15 |
| Cd-23 | Sg-3 | Sg-1 | Sb-11 |
| Cd-24 | Sg-3 | Sg-2 | Sb-11 |
| Cd-25 | Sg-3 | Sg-3 | Sb-18 |
| Cd-26 | Sg-3 | Sg-4 | Sb-1 |
| Cd-27 | Sg-2 | Sg-5 | Sb-7 |
| Cd-28 | Sg-3 | Sg-6 | Sb-7 |
| Cd-29 | Sg-3 | Sg-7 | Sb-6 |
| Cd-30 | Sg-3 | Sg-8 | Sb-6 |
| Cd-31 | Sg-3 | Sg-9 | Sb-12 |
| Cd-32 | Sg-3 | Sg-10 | Sb-14 |
| Cd-33 | Sg-3 | Sg-11 | Sb-17 |
| Cd-34 | Sg-4 | Sg-1 | Sb-18 |
| Cd-35 | Sg-4 | Sg-2 | Sb-15 |
| Cd-36 | Sg-4 | Sg-3 | Sb-7 |
| Cd-37 | Sg-4 | Sg-4 | Sb-7 |
| Cd-38 | Sg-4 | Sg-5 | Sb-6 |
| Cd-39 | Sg-4 | Sg-6 | Sb-1 |
| Cd-40 | Sg-4 | Sg-7 | Sb-1 |
| Cd-41 | Sg-4 | Sg-8 | Sb-11 |
| Cd-42 | Sg-4 | Sg-9 | Sb-11 |
| Cd-43 | Sg-4 | Sg-10 | Sb-2 |
| Cd-44 | Sg-4 | Sg-11 | Sb-3 |
| Cd-45 | Sg-5 | Sg-1 | Sb-1 |
| Cd-46 | Sg-5 | Sg-2 | Sb-1 |
| Cd-47 | Sg-5 | Sg-3 | Sb-11 |
| Cd-48 | Sg-5 | Sg-4 | Sb-11 |
| Cd-49 | Sg-5 | Sg-5 | Sb-6 |
| Cd-50 | Sg-5 | Sg-6 | Sb-6 |
| Cd-51 | Sg-5 | Sg-7 | Sb-7 |
| Cd-52 | Sg-5 | Sg-8 | Sb-7 |
| Cd-53 | Sg-5 | Sg-9 | Sb-9 |
| Cd-54 | Sg-5 | Sg-10 | Sb-12 |
| Cd-55 | Sg-5 | Sg-11 | Sb-14 |
| Cd-56 | Sg-6 | Sg-1 | Sb-1 |
| Cd-57 | Sg-8 | Sg-2 | Sb-1 |
| Cd-58 | Sg-6 | Sg-3 | Sb-11 |
| Cd-59 | Sg-6 | Sg-4 | Sb-11 |
| Cd-60 | Sg-6 | Sg-5 | Sb-6 |
| Cd-61 | Sg-6 | Sg-6 | Sb-6 |
| Cd-62 | Sg-6 | Sg-7 | Sb-7 |
| Cd-63 | Sg-6 | Sg-8 | Sb-8 |
| Cd-64 | Sg-6 | Sg-9 | Sb-9 |
| Cd-65 | Sg-6 | Sg-10 | Sb-12 |
| Cd-66 | Sg-6 | Sg-11 | Sb-15 |
| Cd-67 | Sg-7 | Sg-1 | Sb-11 |
| Cd-66 | Sg-7 | Sg-2 | Sb-11 |
| Cd-69 | Sg-7 | Sg-3 | Sb-18 |
| Cd-70 | Sg-7 | Sg-4 | Sb-1 |
| Cd-71 | Sg-7 | Sg-5 | Sb-7 |
| Cd-72 | Sg-7 | Sg-6 | Sb-7 |
| Cd-73 | Sg-3 | Sg-7 | Sb-6 |
| Cd-74 | Sg-7 | Sg-8 | Sb-6 |
| Cd-75 | Sg-7 | Sg-9 | Sb-12 |
| Cd-76 | Sg-7 | Sg-10 | Sb-14 |
| Cd-77 | Sg-7 | Sg-11 | Sb-17 |
| Cd-76 | Sg-8 | Sg-1 | Sb-18 |
| Cd-79 | Sg-8 | Sg-2 | Sb-15 |
| Cd-80 | Sg-8 | Sg-3 | Sb-7 |
| Cd-81 | Sg-8 | Sg-4 | Sb-7 |
| Cd-82 | Sg-8 | Sg-5 | Sb-6 |
| Cd-83 | Sg-8 | Sg-5 | Sb-1 |
| Cd-84 | Sg-8 | Sg-7 | Sb-1 |
| Cd-85 | Sg-8 | Sg-8 | Sb-11 |
| Cd-86 | Sg-8 | Sg-9 | Sb-11 |
| Cd-87 | Sg-8 | Sg-10 | Sb-2 |
| Cd-88 | Sg-8 | Sg-11 | Sb-3 |

<<Electrolyte>>

The electrolyte used in the production method of this invention, although not specifically limited so far as it can activate the building block A as the reaction intermediate, is preferably an electrolyte that contains at least one of sulfur-containing anion (which means anion that contains sulfur atom, the same will apply hereinafter), phosphorus-containing anion, boron-containing anion or chlorine oxide-based anion; more preferably an electrolyte that contains sulfur-containing anion or chlorine oxide-based anion; and even more preferably an electrolyte that contains sulfur-containing anion. The sulfur-containing anion is exemplified by sulfate-based anion ($XSO_4^-$: X represents a freely-selectable group), sulfonate-based anion ($XSO_3^-$) and fluorosulfonate-based anion (anion of fluorine-containing sulfur oxide). The phosphorus-containing anion is exemplified by phosphate-based anion ($XPO_4^-$), phosphonate-based anion ($XPO_3^-$), phosphinate-based anion ($XPO_2^-$) and fluorophosphate-based anion (anion of fluorine-containing phosphorus oxide). The boron-containing anion is exemplified by borate anion ($XBO_3^-$), metaborate-based anion ($XBO_2^-$) and fluoroborate-based anion (anion of fluorine-containing boron oxide). The chlorine oxide-based anion is exemplified by perchlorate anion ($ClO_4^-$), chlorate anion ($ClO_3^-$) and chlorous anion ($ClO_2^-$).

In a case where the electrolyte contains the sulfur-containing anion or the phosphorus-containing anion, these anions preferably have an alkyl group (may be any of straight-chain, branched or cyclic), aryl group, fluorine atom or chlorine atom, bound to sulfur atom or phosphorus atom; and more preferably have straight-chain or branched alkyl group or fluorine atom, bound to sulfur atom or phosphorus atom. The alkyl group is also preferably fluorinated. The number of carbon atoms of the alkyl group is preferably 1 to 6, more preferably 1 to 4, and even more preferably 1 or 2.

In particular, the electrolyte preferably contains an anion represented by Formula (E1) below.

$$X^1S(=O)_2(-O)^- \qquad \text{Formula (E1)}$$

In Formula (E1), $X^1$ represents a fluorine atom, chlorine atom or straight-chain or branched alkyl group, and preferably represents a fluorine atom or straight-chain or branched fluoroalkyl group. Now, the number of carbon atoms of the alkyl group is preferably 1 to 4, more preferably 1 or 2, and even more preferably 1. The fluoroalkyl group is preferably perfluoroalkyl group. In particular, $X^1$ preferably represents a fluorine atom, or, straight-chain perfluoroalkyl group having 1 to 4 carbon atoms; more preferably represents a fluorine atom or trifluoromethyl group; and particularly preferably trifluoromethyl group.

The anion represented by Formula (E1) is specifically exemplified by triflate anion ($CF_3SO_3^-$), fluorosulfonate anion ($FSO^{3-}$) and nonaflate anion ($C_4F_9SO_3^-$), among which triflate anion or fluorosulfonate anion is preferred, and triflate anion is more preferred.

Meanwhile, anions other than those represented by Formula (E1) are exemplified by perchlorate anion ($ClO_4^-$), tetrafluoroborate anion ($BF_4^-$), and tetraphenyl (Ph) borate anion ($BPh_4^-$), among which perchlorate anion ($ClO_4^-$) is preferred.

Moreover, the electrolyte used in the production method of this invention may contain, for example, ammonium-based, imidazolium-based, pyridinium-based or phosphonium cation, among which ammonium-based or phosphonium-based cation is preferably contained, and particularly, a quaternary ammonium-based or quaternary phosphonium-based cation represented by Formula (E2) below is preferably contained.

$$(R^E)_4(X^2)^+ \quad \text{Formula (E2)}$$

In Formula (E2), $X^2$ preferably represents a nitrogen atom or phosphorus atom. Nitrogen atom is preferred.

Each $R^E$ independently represents an optionally substituted hydrocarbon group. The individual ($R^E$)s may be same or different, and preferably all in the same type. The individual ($R^E$)s may bind to each other to form a ring. Moreover, $R^E$ is preferably a $C_{1-10}$ hydrocarbon group or a $C_{1-10}$ perfluorohydrocarbon group.

In particular, $R^E$ is preferably an alkyl group (may have any of straight-chain, branched or cyclic structure), phenyl group, benzyl group, or, alkylenoxy group having one or more independent alkyl chains. The alkyl group is preferably a straight-chain or branched alkyl group, with a number of carbon atoms of preferably 1 to 8, more preferably 1 to 6, and even more preferably 1 to 4. Now, the "independent alkyl chain" having described regarding the alkylenoxy group means each alkyl chain isolated by an oxygen atom, exemplifying that "$CH_3OCH_2$" has two independent alkyl chains. The number of independent alkyl chains is preferably 1 to 10, and more preferably 2 to 8. The number of carbon atoms of each alkyl chain is preferably 1 to 5, and is more preferably 2 or 3. The group $R^E$ is also preferably a perfluorinated group of the hydrocarbon group, or a polyalkylene glycol group having a number of repetitions of 2.

More specifically, $R^E$ preferably represents a methyl group, ethyl group, propyl group, butyl group, pentyl group, hexyl group, cyclohexyl group, methoxymethyl group, 2-methoxyethoxymethyl group or nonafluorobutyl group, among which butyl group is preferred.

More specifically, the cation represented by Formula (E2) is preferably a tetramethylammonium cation (($CH_3)_4N^+$), tetrabutylammonium cation (($C_4H_9)_4N^+$), dimethyl (dimethoxymethyl) ammonium cation (($CH_3)_2(CH_3OCH_2)_2N^+$), tetramethylphosphonium cation (($CH_3)_4P^+$), tetrabutylphosphonium cation (($C_4H_9)_4P^+$), or tetraphenylphosphonium cation ($Ph_4P^+$), among which tetramethylammonium cation or tetrabutylammonium cation is preferred, and tetrabutylammonium cation is particularly preferred.

The electrolyte used in the production method of this invention preferably contains the anion and the cation having been enumerated as the preferred embodiments. Preferred combinations of the anion and the cation are exemplified by combination of triflate anion and tetrabutylammonium cation, combination of fluorosulfonate anion and tetrabutylammonium cation, and combination of perchlorate anion and tetrabutylammonium cation, among which preferred is combination of triflate anion and tetrabutylammonium cation. Only one kind, or combination of two or more kinds of electrolyte may contain the anion, and only one kind, or combination of two or more kinds of electrolyte may contain the cation.

In this invention, molar ratio of the sugar acceptor to the sugar donor in the reaction system preferably falls within the range from 1 to 3, and more preferably within the range from 1 to 1.2. Meanwhile, molar ratio of the electrolyte, to be applied to the reaction liquid during production, to the sugar donor preferably falls within the range from 1.1 to 10, and more preferably from 2 to 5.

<<Aprotic Organic Solvent>>

The aprotic organic solvent may be any of organic solvent not specifically limited, so far as it is less likely to donate proton ($H^+$), and can dissolve the electrolyte, and is preferably free of hydroxy group (—OH), amino group (—$NH_2$, —NHR, where R represents an organic group), and nitro group (—$NO_2$). The aprotic organic solvent may be either non-polar solvent with relatively small polarity, or polar solvent with relatively large polarity. Among the aprotic organic solvent, usable examples of the non-polar solvent include hydrocarbons such as hexane, benzene and toluene; highly symmetric ethers (for example, diethyl ether with a point-symmetrical structure), chloroform and methylene chloride; meanwhile the usable examples of the polar solvent include acetone, N-methylpyrrolidone, ethyl acetate, acetonitrile, ethers other than those enumerated above (for example, tetrahydrofuran, etc.), dimethyl sulfoxide (DMSO) and dimethylformamide (DMF). The aprotic organic solvent preferably contains at least one of hexane, benzene, toluene, methylene chloride or acetonitrile, and more preferably contains methylene chloride. Only one kind of, or combination of two or more kinds of the aprotic organic solvent may be used.

Note that the aprotic organic solvent may contain a solvent other than the aprotic organic solvent, for the purpose of controlling pH of the reaction liquid, or current density during the electrolytic oxidation. Such solvent is exemplified by protic organic solvent. Alcohol and nitromethane, for example, are usable as the protic organic solvent, wherein alcohol is preferably used. The alcohol is preferably at least one of hexafluoroisopropanol or trifluoroethanol. Content of the solvent other than the aprotic organic solvent is preferably 0 to 50% by mass relative to the total content of solvent, more preferably 0 to 30% by mass, and even more preferably 0 to 10% by mass.

<<Electrolytic Oxidation and Glycosylation>>

A process involving electrolytic oxidation and glycosylation includes energizing step a for energizing a composition that contains the building block A and the electrolytic solution and the aprotic organic solvent (referred to as "reaction liquid", hereinafter); addition step b for adding a composition that contains the building block B and the aprotic organic solvent (referred to as "addition liquid", hereinafter); and, acceleration step c for accelerating glycosylation of these building blocks. The glycan may be scaled up by repeating a sequence of these three steps, combined as one cycle, multiple times. The number of repetition of the cycled sequence may properly be determined without special limitation, depending on a target length of the glycan. For example, the cycle repeated twice will suffice to produce a trisaccharide glycan from monosaccharide building blocks A and B, and the cycles repeated three times will suffice to produce a tetrasaccharide glycan. Kind of building block B to be added may be changed when repeating the cycle. For example, kind of protective group for hydroxy group may be changed, or position of carbon atom on which a hydroxy group binds may be changed. Such change of the position of carbon atom on which a hydroxy group binds is beneficial for a case where the bond form is desired to be changed in the middle of glycan. The production method of this invention, benefited by improved yield ratio of glycan, can fully demonstrate its advantage when elongating the glycan, and can achieve a yield ratio markedly superior to that in the prior method, even in a case where trisaccharide or longer polysaccharide is obtained as a deliverable.

Since the glycan can be elongated in this invention simply by repeating the cycled sequence, so that the number of sugar residues composing the target glycan is not specifically limited. From the viewpoint of avoiding degraded yield ratio and applications, the number of sugar residues composing the glycan is preferably 10 or smaller, more preferably 8 or smaller, even more preferably 6 or smaller, and yet more preferably 5 or smaller.

Moreover, these steps may be carried out in a temporarily separated manner, or in a partially overlapped manner. For example, the building block B may be added while optionally energizing the reaction liquid, or may be added under heating. From the viewpoint of improving the yield ratio, these steps are preferably carried out in a temporarily separated manner.

In the energizing step a, the building block A as the sugar donor is activated by electrolytic oxidation, whereby the reaction intermediate is produced and accumulated. Energization intensity, although not specifically limited, is preferably around 1 to 100 mA, more preferably 2 to 20 mA, and even more preferably 4 to 12 mA. Electric charge may be properly determinable typically depending on the number of moles or oxidation potential of raw material, whose lower limit is preferably around 0.7 F/mol or above and more preferably 1.0 F/mol or above, meanwhile whose upper limit is preferably 3.0 F/mol or below and more preferably 1.5 F/mol or below. Temperature of the reaction liquid during energization is preferably −50° C. or lower, more preferably −60° C. or lower, and even more preferably −70° C. or lower. The lower limit of the temperature is preferably, for example, −100° C. or above, and may also be −90° C. or above.

In the addition step b, the building block B as the sugar acceptor is added to the reaction liquid. Concentration of the building block B in the reaction liquid is preferably 0.1 to 2.0 mol/L, and more preferably 0.2 to 0.5 mol/L. The sugar acceptor is preferably added slowly over a certain period of time, from the viewpoint of homogeneity of reaction. Rate of addition of the addition liquid is preferably, for example, 0.1 to 2.0 mL/min, and more preferably 0.5 to 1.0 mL/min. The organic solvent usable here may be the aprotic organic solvent usable for the reaction liquid, and is preferably same as the solvent actually used for the reaction liquid.

In the acceleration step c with the reaction liquid kept heated and thus maintained for a certain period of time, an active site of the building block A having been activated by the electrolytic oxidation is allowed to react with hydroxy group of the building block B, whereby glycosylation proceeds. Temperature at which the reaction liquid is kept heated is preferably −70 to −40° C., and more preferably −65 to −45° C. Rate of elevating temperature and rate of lowering temperature, although not specifically limited, are preferably 0.5 to 5° C./min, and more preferably 1 to 3° C./min.

<<System Etc., for Implementing Production Method of Invention>>

The production method of this invention, by which glycosylation can electrochemically proceed, is highly appreciated in terms of safety and environmental concerns, since the method can achieve work safety, almost without production of hazardous wastes such as metal oxidant residue. Concurrently, the production method of this invention is advantageous also in terms of cost which is emphasized in industrial production. The production method of this invention is most suitable for one-pot synthesis of stereoselective glycan with use of an automated liquid phase electrolytic synthesis system. This, however, does not preclude any manual operation of a partial process for isolating or purifying the product, in the individual steps of elongating the glycan. Alternatively, all steps in the glycan synthesis may be implemented manually. For glycan synthesis with use of the automated liquid phase electrolytic synthesis system, the synthesis will be smoothly started by preliminarily preparing, as a kit, the composition that contains the building block A and the electrolytic solution and the aprotic organic solvent, and a composition that contains the building block B and the aprotic organic solvent.

<Compounds>

A first compound in this invention is a compound represented by Formula (3) below.

[Chemical Formula 33]

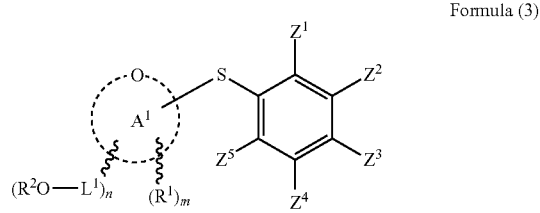

Formula (3)

In Formula (3), $A^1$ represents a cyclic structure having 4 to 8 carbon atoms, each of $Z^1$ to $Z^5$ independently represents a hydrogen atom or an electron attractive group, with the total of the Hammett's σ values of $Z^1$ to $Z^5$ exceeding 0.12, $L^1$ represents a single bond or a divalent linking group, $R^1$ represents a phthalimido group, azido group, ($C_{1-10}$ alkyloxy)$_n$ group (n represents an integer from 1 to 5), $C_{1-10}$ alkylcarbonyl group, $C_{1-10}$ alkylcarbonyloxy group, $C_{1-10}$ alkylamido group or tri ($C_{1-5}$ alkylsiloxy) group, $R^2$ represents a $C_{1-10}$ alkyl group, $C_{1-10}$ alkyl carbonyl group, ($C_{1-10}$ alkyloxy)$_n$-$C_{1-10}$ alkyl group (n represents an integer from 1 to 4) or tri ($C_{1-5}$ alkylsilyl) group, each of m ($R^1$)s and n ($R^2$)s may bind to each other to form a ring, m represents an integer of 0 or larger, n represents an integer of 1 or larger, m+n is equal to or smaller than the number of carbon atoms of the cyclic structure $A^1$, each wavy line independently represents a bond in the equatorial or axial conformation, and a bond between $A^1$ and sulfur atom is in the equatorial conformation.

A second compound in this invention is a compound represented by Formula (4) below.

[Chemical Formula 34]

Formula (4)

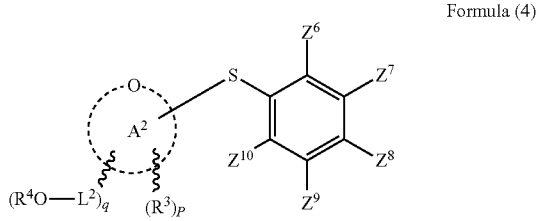

In Formula (4), $A^2$ represents a cyclic structure having 4 to 8 carbon atoms, each of $Z^6$ to $Z^{1}c$ independently represents a hydrogen atom or an electron attractive group, with the total of the Hammett's σ values of $Z^6$ to $Z^{10}$ exceeding 0.12, $L^2$ represents a single bond or a divalent linking group, $R^3$ represents a phthalimido group, azido group, $(C_{1-10}$ alkyloxy$)_n$ group (n represents an integer from 1 to 5), $C_{1-10}$ alkyl carbonyl group, $C_{1-10}$ alkylcarbonyloxy group, $C_{1-10}$ alkylamido group or tri $(C_{1-5}$alkylsiloxy) group, $R^4$ represents a hydrogen atom, $C_{1-10}$ alkyl group, $C_{1-10}$ alkylcarbonyl group, $(C_{1-10}$ alkyloxy$)_n$-$C_{1-10}$ alkyl group (n represents an integer from 1 to 4) or tri$(C_{1-5}$ alkylsilyl) group, at least one of q $(R^4)$s represents a hydrogen atom, each of p $(R^3)$s and q $(R^4)$s may bind to each other to form a ring, p represents an integer of 0 or larger, q represents an integer of 1 or larger, p+q is equal to or smaller than the number of carbon atoms of the cyclic structure $A^2$, each wavy line independently represents a bond in the equatorial or axial conformation, and a bond between $A^2$ and sulfur atom is in the equatorial conformation.

In Formula (3), the cyclic structure $A^1$ beneficially contains only one oxygen atom in the cyclic structure, from the viewpoints of formation of the glycosidic bond at a desired site and of applications, and preferably has a pyranose ring in which five carbon atoms and one oxygen atom occupy the vertices to form a six-membered ring, or a furanose ring in which four carbon atoms and one oxygen atom occupy the vertices to form a five-membered ring. Preferred embodiments of $R^1$ are same as those for $R^1$ in Formula (1). $R^1$ is preferably unsubstituted, whose particularly preferred examples include phthalimido group, azido group, acetyloxy group, acetamido group, benzyloxy group, benzoyloxy group, methoxy group, ethoxy group, methoxymethyloxy group and trimethylsiloxy group.

$L^1$ preferably represents a single bond, or, an optionally substituted $C_{1-5}$ alkylene group, wherein more preferred is single bond, methylene group or ethylene group. m is preferably 1 to 3, more preferably 1 or 2, and even more preferably 1. Each of m $(R^1)$s may independently represent the organic group. If m is 2 or larger, the (R')s may be the same organic group, or may be different organic groups. $R^2$ is preferably unsubstituted similarly to $R^2$ in Formula (1), whose particularly preferred examples include methyl group, ethyl group, acetyl group, trimethylacetyl group, benzyl group (for example, p-methoxybenzyl group, p-methylbenzyl group), benzoyl group, trimethylsilyl group and t-butyldimethylsilyl group. n is preferably an integer from 2 to "the number of carbon atoms in cyclic structure $A^1$-2", and more preferably 2 or 3. Each of n $(R^2O-L^1)$s may independently represent the aforementioned organic group, and if n is 2 or larger, the organic groups may be same or different.

Preferred combinations of $Z^1$ to $Z^5$ have been typically enumerated as Sb-1 to Sb-18, similarly to the case of $Z^1$ to $Z^5$ in Formula (1). Meanwhile, also preferred specific examples of the building block represented by Formula (3) are same as the preferred specific examples of the building block represented by Formula (1) (compounds No. Ca-1 to Ca-80), which have been listed in the aforementioned table.

In Formula (4), the cyclic structure $A^2$ beneficially contains only one oxygen atom in the cyclic structure, from the viewpoints of formation of the glycosidic bond at a desired site and of applications, and preferably has a pyranose ring in which five carbon atoms and one oxygen atom occupy the vertices to form a six-membered ring, or a furanose ring in which four carbon atoms and one oxygen atom occupy the vertices to form a five-membered ring. Preferred embodiments of $R^3$ are same as those for $R^1$ in Formula (1). $R^3$ is preferably unsubstituted, whose particularly preferred examples include phthalimido group, azido group, acetyloxy group, acetamido group, benzyloxy group, benzoyloxy group, methoxy group, ethoxy group, methoxymethyloxy group and trimethylsiloxy group.

$L^2$ preferably represents a single bond, or, an optionally substituted $C_{1-5}$ alkylene group, wherein more preferred is single bond, methylene group or ethylene group. p is preferably 1 to 3, more preferably 1 or 2, and even more preferably one. Each of p $(R^3)$s may independently represent the organic group. If p is 2 or larger, the $(R^3)$s may be the same organic group, or may be different organic groups. $R^4$ is preferably unsubstituted similarly to $R^2$ in Formula (1), whose particularly preferred examples include methyl group, ethyl group, acetyl group, trimethylacetyl group, benzyl group (for example, p-methoxybenzyl group, p-methylbenzyl group), benzoyl group, trimethylsilyl group and t-butyldimethylsilyl group. q is preferably an integer from 2 to "the number of carbon atoms in cyclic structure $A^2$-2", and more preferably 2 or 3. Each of q $(R^4O-L^2)$s may independently represent the aforementioned organic group, and if q is 2 or larger, the organic groups may be same or different.

Preferred combinations of $Z^6$ to $Z^{10}$ have been typically enumerated as Sb-1 to Sb-18, similarly to the case of $Z^1$ to $Z^5$ in Formula (1). Meanwhile, also preferred specific examples of the building block represented by Formula (4) are same as the preferred specific examples of the building block represented by Formula (2) (compounds No. Cb-1 to Cb-80), which have been listed in the aforementioned table.

A third compound of this invention is a compound represented by Formula (5) below.

[Chemical Formula 35]

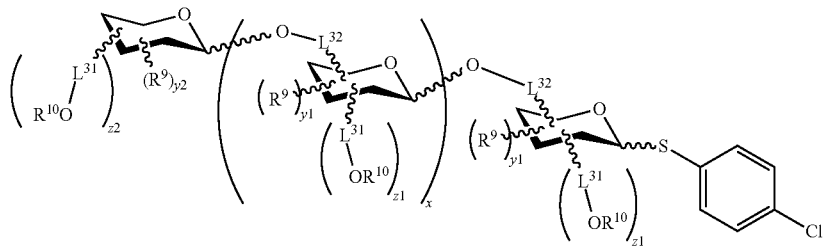

Formula (5)

In Formula (5),
each of $L^{31}$ and $L^{32}$ independently represents a single bond, methylene group or ethylene group;
each $R^9$ independently represents a phthalimido group, azido group, acetyloxy group, acetamido group, benzyloxy group or benzoyloxy group;
each $R^{10}$ independently represents a hydrogen atom, methyl group, ethyl group, acetyl group, trimethylacetyl group, benzyl group or benzoyl group;
x represents an integer from 0 to 10,
each of y1 and y2 independently represents an integer from 0 to 2;
each z1 independently represents an integer of 2 or 3;
z2 represents an integer from 2 to 4;
y1+z1=3, and y2+z2=4 hold; and
each wavy line independently represents a bond in the equatorial or axial conformation.

The third compound of this invention may be produced by subjecting the first compound and the second compound of this invention to the glycosilation reaction. x is controllable, as described previously, by increasing or decreasing the number of repetition of glycosylation of the building blocks. For production of oligosaccharide, x is around 0 to 10, and may be 0 to 7, with the lower limit set to 1 or above, or 2 or above, and with the upper limit set to 5 or below, or 4 or below, or 3 or below.

$R^9$ is preferably unsubstituted similarly, for example, to $R^1$ in Formula (1), whose particularly preferred examples include phthalimido group, azido group, acetyloxy group, acetamido group, benzyloxy group, benzoyloxy group, methoxy group, ethoxy group, methoxymethyloxy group and trimethylsiloxy group. Each of y1 and y2 is preferably 1 to 3, more preferably 1 or 2, and even more preferably one. Each $R^9$ may independently represent the organic group. If each of y1 and y2 is 2 or larger, the ($R^9$)s may be the same organic group, or may be different organic groups. $R^{10}$ is preferably unsubstituted similarly, for example, to $R^2$ in Formula (1), whose particularly preferred examples include methyl group, ethyl group, acetyl group, trimethylacetyl group, benzyl group (for example, p-methoxybenzyl group, p-methylbenzyl group), benzoyl group, trimethylsilyl group and t-butyldimethylsilyl group. z1 preferably represents an integer of 2 or 3, and more preferably 2. z2 preferably represents an integer from 2 to 4, more preferably 3 or 4, and even more preferably 3. Each $R^{10}O$-$L^{31}$ may independently represent the organic group. If each of z1 and z2 is 2 or larger, the ($R^{10}O$-$L^{31}$)s may be the same organic group, or may be different organic groups.

A bond between sulfur atom and carbon atom is preferably in the equatorial conformation.

<<Method for Synthesizing Compound>>

The first compound of this invention is a thioglycoside having a "first-position carbon-sulfur" bond, and is synthesizable for example by using a monosaccharide having a desired cyclic structure such as glucose, and thiophenol having a desired phenyl group, and by allowing them to react so that the thiol group will bind to the first-position carbon of the monosaccharide. These sorts of monosaccharide and thiophenol are not specifically limited so far as they have a desired cyclic structure and a desired phenyl group. Any commercially available compounds are applicable to such monosaccharide and thiophenol. The reaction between the monosaccharide and thiophenol is preferably carried out after blocking the hydroxy group of the monosaccharide with a protective group such as acetyl group. Alternatively, a commercially available monosaccharide having the hydroxy group preliminarily blocked (for example, penta-O-acetyl-β-D-glucopyranose, from Tokyo Chemical Industry Co., Ltd.) may be used. In this invention, a specific method for allowing the monosaccharide to react with thiophenol is properly selectable from known methods, without special limitation. Such method is exemplified by a method by which the monosaccharide and thiophenol are allowed to react, for example, in an aprotic organic solvent, in the presence of a Lewis acid such as boron trifluoride etherate. Temperature of this reaction is preferably set, for example, to 0 to 50° C., although not specifically limited. By such method, obtainable is a monosaccharide having a thiophenol residue bound to the first-position carbon, and having all of, or part of hydroxy groups blocked. Also a method for separating the thus obtained monosaccharides into α-form (having sulfur atom in the axial conformation) and β-form (having sulfur atom in the equatorial conformation) may properly be selected from known methods, without special limitation.

The second compound of this invention is obtainable by using the first compound of this invention as a raw material, and by deblocking all of, or selectively a part of the hydroxy groups.

Method for blocking and deblocking the hydroxy groups in the first compound and the second compound of this invention is selectable from known methods typically based on dehydration condensation reaction, hydrolysis reaction, oxidation reaction and reduction reaction (for example, methods described in "Protective Groups in Organic Synthesis, Fourth Edition"), and from equivalent methods, without special limitation. In particular, the methods for selectively blocking and deblocking a part of hydroxy groups may be implemented for example by using a bulky protective group; by using a combination of protective groups capable of causing addition or elimination under different acidic/basic conditions; or by blocking a plurality of hydroxy groups with a multivalent protective group such as diol, and then by deblocking a part of them. Specific methods for selective blocking and deblocking, which differ depending on types of sugar and protective group, are properly selectable from known methods.

An exemplary selective unblocking will be explained below, referring to a case where the second compound of this invention is obtained from the first compound having been synthesized by using glucopyranose as the monosaccharide. First, the protective group of glucopyranose is deblocked. The deblocking process is properly selectable from known methods, depending on kinds of the protective group. For example, acetyl group when used as the protective group may be removed by an ester hydrolysis reaction under an acidic condition, in an appropriate organic solvent (methanol, for example). Next, the organic solvent is evaporated off, an acetonitrile solution of the thus deblocked monosaccharide is prepared, and benzaldehyde dimethyl acetal is then added to the acetonitrile solution kept stirred at room temperature (23° C.). This selectively protects the hydroxy groups on the fourth position and the sixth position of monosaccharide with a benzylidene acetal group. Acetonitrile is then evaporated off to obtain the monosaccharide in a solid form, the solid is dissolved in a mixed solution of methylene chloride and pyridine, acetic anhydride and DMAP (4-dimethylaminopyridine) are added to the solution, and the mixture is thoroughly stirred at room temperature. This introduces an acetyl group as the protective group, to the hydroxy group on the third-position. To the solution, hydrogen chloride is added in the presence of sodium cyanoborohydride, selectively causing ring opening of 4,6-O-benzylidene acetal, whereby obtainable is the second compound with a hydroxy group on the sixth position kept unblocked.

<<Applications of Compound>>

The compound of this invention is usable, as described previously, as the building block for glycan synthesis.

EXAMPLES

This invention will further specifically be explained below referring to Examples. Note that materials, amounts of consumption, ratios, processing details, and processing procedures described in Examples below may properly be modified without departing from the spirit of this invention. Hence, the scope of this invention is not limited by the specific examples described below. "Part(s)" and "%" are on the mass basis unless otherwise specifically noted.

Example 1

<<Raw Materials for Glycan Synthesis>>

Raw materials used here are as follows.

Sugar donor: Building block 1a shown below (total of σ values=0.23)

[Chemical Formula 36]

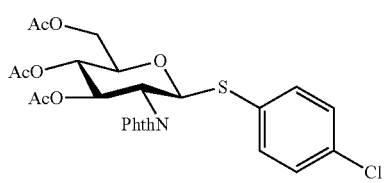

(1a)

Sugar acceptor: Building block 2a shown below (total of σ values=0.23)

[Chemical Formula 37]

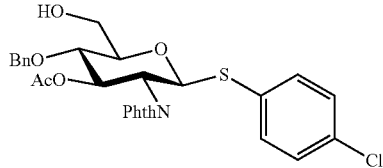

(2a)

Electrolyte: Tetrabutylammonium triflate (Bu$_4$NOTf)

Aprotic organic solvent: Methylene chloride (CH$_2$Cl$_2$)

<<Synthesis of Building Blocks>>

Methods for synthesizing the building blocks 1a and 2a used in Examples will be explained referring to Reaction Formula (S3) below.

Into methylene chloride (74 mL), introduced were 3,4,6-tri-O-acetyl-2-deoxy-2-phthalimido-β-D-gluocopyranoside (23.9 g) and 4-chlorothiophenol (8.7 g), and boron trifluoride etherate (10.6 g). The reaction liquid was kept at 50° C. under stirring for 48 hours, so as to allow the glucopyranoside and the thiophenol to react. After completion of the reaction, the reaction liquid was neutralized with a base (saturated aqueous sodium bicarbonate solution used in this Example), a solid matter was removed by filtration through celite, followed by extraction based on liquid separation with ethyl acetate, to obtain a crude product. The crude product was then recrystallized from ethyl acetate to obtain a monosaccharide, which is the building block 1a in the form of colorless crystal (first stage in Reaction Formula (S3), yield ratio=98%, yield amount=27.5 g).

The building block 1a was then used as a starting material, to synthesize the building block 2a according to the second to fourth stages in Reaction Formula (S3) below. First, the building block 1a (22.4 g) was dissolved in methanol (130 mL), a 2.0 M hydrogen chloride solution in diethyl ether (40 mL) was added to the methanol solution, and the mixture was stirred at room temperature for 18 hours. The solvent was evaporated off from the solution under reduced pressure, and the residue was dried in vacuo. The obtained while solid was put into acetonitrile solvent (215 mL), benzaldehyde dimethyl acetal (22 mL) was further added to the acetonitrile solution, and the mixture was stirred at room temperature for 4 days. The solvent was evaporated off, and the residual solid was purified by silica gel column chromatography (hexane:ethyl acetate=2:1, used as an eluent), to obtain an intermediate 1 (18.6 g) (second stage, yield ratio=89%). The intermediate 1 (52.9 g) was then dissolved in a mixed solvent of methylene chloride and pyridine (450 mL, methylene chloride:pyridine=3:1 (v/v)), to which acetic anhydride (Ac$_2$O, 61 mL) and DMAP (1.3 g) were added, to acetylate a hydroxy group on the third position. The monosaccharide was then recrystallized from ethyl acetate, to obtain an intermediate 2 (52.3 g, yield ratio=91%) (third state). The obtained intermediate 2 (3.0 g) was added to a mixed solvent of trimethylsilyl triflate (1.4 mL) and borane-THF (tetrahydrofuran) complex (14 mL), and the mixed solvent was stirred on an ice bath for 7 hours. The reaction was then terminated by adding appropriate amounts of methanol and triethylamine, a solid matter was removed by filtration through celite, followed by extraction based on liquid separation with ethyl acetate, to obtain a crude product. The crude product was then purified by silica gel column chromatography (mixed solvent of hexane:ethyl acetate=2:1 (v/v), used as an eluent), to obtain the building block 2a (fourth stage, yield ratio=64%, yield amount=1.9 g).

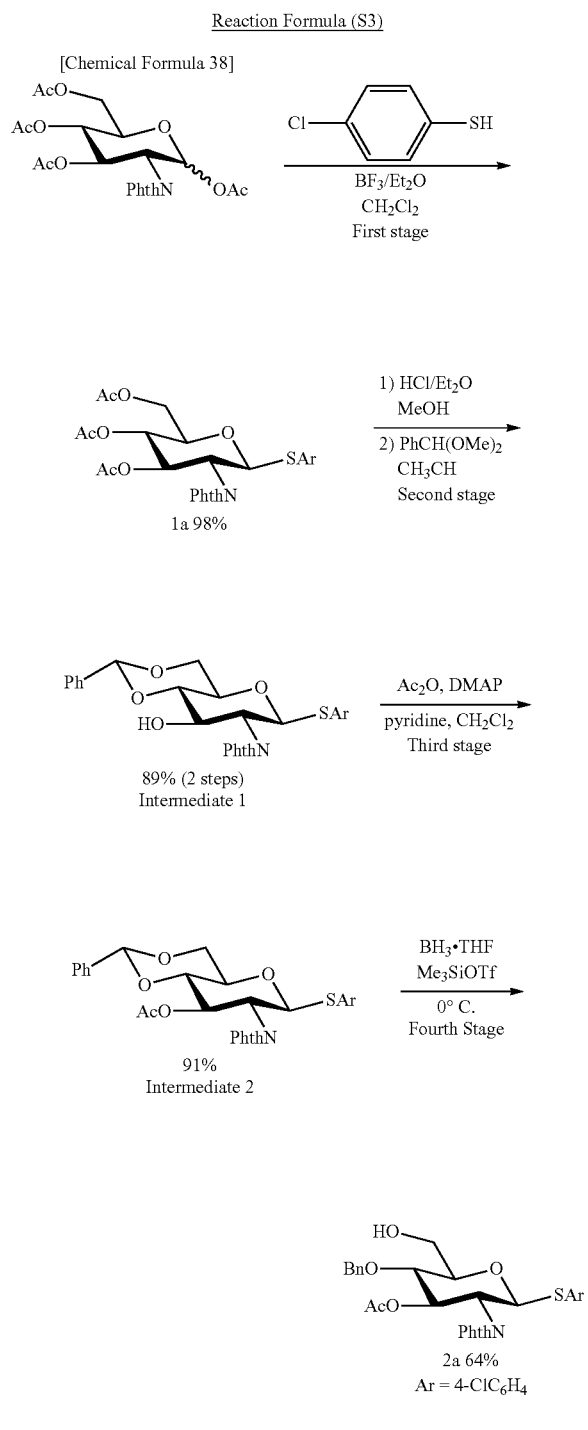

<<Electrolytic Oxidation and Glycosylation>>

FIG. 1 illustrates a graph of a part of synthetic sequence in Example 1. First, an H-type electrolytic cell (16 mL per chamber) with a glass separation membrane was heated, dried under reduced pressure, and replaced the inside atmosphere of the electrolytic cell with argon. Next, tetrabutylammonium triflate (1.6 mmol, 626 mg) and methylene chloride (16 mL) were placed in both of a positive electrode chamber and a negative electrode chamber of the electrolytic cell. The building block 1a (0.40 mmol, 225 mg) was added to the positive electrode chamber, and trifluoromethanesulfonic acid (0.80 mmol, 120 mg) was added to the negative electrode chamber, the electrolytic cell was cooled in a cold bath set to −80° C., and the reaction liquid was kept stirred.

Approximately 10 minutes after, the electrolytic cell was started to be energized (6.0 mA), and was kept energized for one hour and 47 minutes so as to adjust the electric charge to 1.0 F/mol (Step a in FIG. 1). After completion of energization, the whole amount of a methylene chloride solution (1.0 mL) of the building block 2a (0.40 mmol, 227 mg) was added to the reaction liquid, by using a syringe pump at a rate of 1.0 mL/min (Step b in FIG. 1). After completion of addition, the temperature of the cold bath was elevated to −50° C. at a rate of 2° C./min, kept at −50° C. for 30 minutes, and then lowered again to −80° C. at a rate of 2° C./min (Step c in FIG. 1).

Steps a to c, collectively assumed as one cycled sequence, were repeated again. After completion of the cycled sequence, triethylamine (0.20 mL) was added to the reaction liquid to terminate the reaction, and the reaction liquid was kept stirred for approximately 10 minutes while keeping the temperature unchanged. Next, the electrolytic cell was taken out from the cold bath, and, after confirming that the temperature returned back to room temperature, the reaction liquid in both electrode chambers was transferred to an eggplant flask, and the solvent was removed from the reaction liquid by using an evaporator and a vacuum pump. A residue remained after evaporation was then purified for the first time through a silica gel column with use of a solvent. The solvent used here was a mixture of hexane/ethyl acetate (EtOAc), whose volume ratio was set initially to 2:1, and then changed from the middle to 1:1 after confirming elution of a target product. After purification for the first time, the solvent in the solution was evaporated off by using an evaporator, followed by drying in vacuo, to obtain 450 mg of a crude product. The crude product was then allowed to pass again through the silica gel column with use of a solvent for purification for the second time. Also the solvent at this time was a mixture of hexane/ethyl acetate (EtOAc), whose volume ratio was kept to 1:1 throughout the process. After purification for the second time, the solvent in the solution was evaporated off by using an evaporator, followed by drying in vacuo, to obtain a target trisaccharide (compound 3a shown below, 0.28 mmol, 390 mg). Yield ratio of the trisaccharide 3a was found to be 69%. The reaction is given by Reaction Formula (S4).

Reaction Formula (S4)

[Chemical Formula 39]

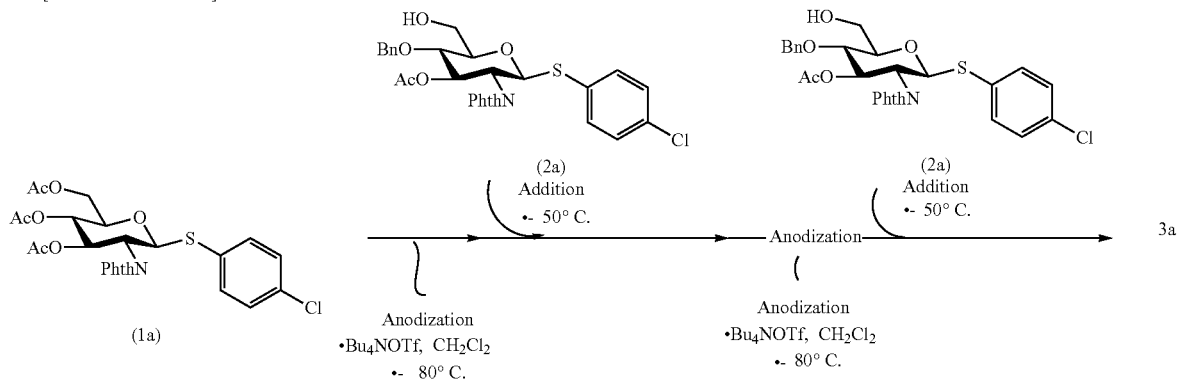

[Chemical Formula 40]

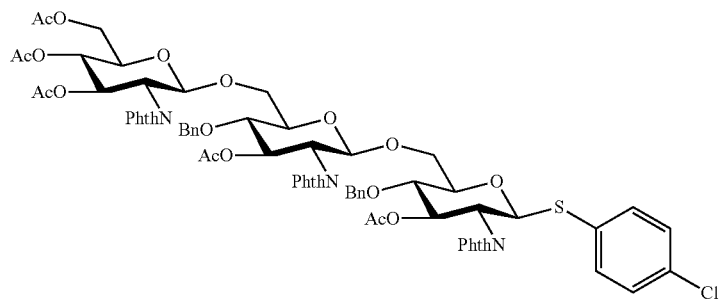

Results of NMR analysis of the trisaccharide 3a are shown below.

[Chemical Formula 41]

TLC (hexane/EtOAc 1:1): Rf 0.50.

<$^1$H NMR (CDCl$_3$, 600 MHz) Chemical Shifts>

7.84-7.78 (m, 4H), 7.73-7.67 (m, 6H), 7.59-7.56 (m, 2H), 7.30-7.24 (m, 7H), 7.23-7.19 (m, 3H), 7.10-7.08 (m, 2H), 7.01-6.99 (m, 2H), 5.80 (dd, J=10.8, 9.0 Hz, 1H), 5.67 (dd, J=10.8, 9.0 Hz, 1H), 5.62 (dd, J=10.2, 9.6 Hz, 1H), 5.57 (d, J=8.4 Hz, 1H), 5.51 (d, J=10.2 Hz, 1H), 5.42 (d, J=8.4 Hz, 1H), 5.17 (pseudo –t, J=9.6 Hz, 1H), 4.45-4.39 (m, 3H), 4.354 (d, J=11.4 Hz, 1H), 4.346 (dd, J=12.0, 4.2 z, 1H), 4.205 (d, J=11.4 Hz, 1H), 4.204 (dd, J=10.8, 2.4 Hz, 1H), 4.17 (dd, J=12.0, 2.4 Hz, 1H), 4.12 (dd, J=11.4, 1.2 Hz, 1H), 4.09 (dd, J=10.8, 1.8 Hz, 1H), 3.99 (pseudo –t, J=10.2 Hz, 1H), 3.90-3.85 (m, 2H), 3.68-3.64 (m, 2H), 3.59 (pseudo –t, J=9.6 Hz, 1H), 3.55 (ddd, J=9.6, 4.2, 1.8 Hz, 1H), 3.40 (pseudo –t, J=9.6 Hz, 1H), 2.08 (s, 3H), 1.99 (s, 3H), 1.86 (s, 3H), 1.73 (s, 3H), 1.59 (s, 3H).

<$^{13}$C NMR (CDCl$_3$, 150 MHz) Chemical Shifts>

δ 170.8, 170.2, 170.04, 169.95, 169.5, 167.8, 167.1, 137.6, 137.5, 134.9, 134.6, 134.4, 134.2, 131.7, 131.5, 131.1, 129.1, 128.4, 128.3, 128.2, 127.9, 127.7, 127.6, 127.5, 123.7, 123.54, 123.47, 98.1, 97.8, 81.8, 78.1, 76.5, 74.8, 74.60, 74.56, 73.8, 73.1, 72.0, 70.8, 68.9, 67.9, 67.7, 62.0, 54.9, 54.9, 54.6, 53.7, 20.8, 20.6, 20.52, 20.49, 20.4.

HRMS (ESI) m/z calcd for C$_{72}$H$_{66}$ClN$_3$NaO$_{23}$S [M+Na]$^+$, 1430.3389; found 1430.3351.

Comparative Example 1

The glycan synthesis was conducted according to the sequence same as in Example 1, except that building blocks listed below were used as the sugar donor and as the sugar acceptor. As a consequence, a trisaccharide 3r (0.094 mmol, 131 mg) shown below was obtained. Yield ratio of the trisaccharide 3r was found to be 24%. Note that the building blocks 1r and 2r were synthesized according to procedures same as in Example 1, except that 4-fluorothiophenol was used in place of 4-chlorothiophenol.

Sugar donor: Building block 1r shown below (total of σ values=0.06)

[Chemical Formula 42]

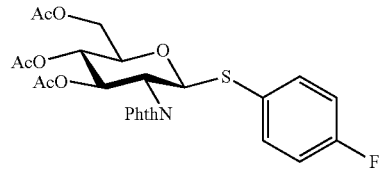

Sugar acceptor: Building block 2r shown below (total of σ values=0.06)

[Chemical Formula 43]

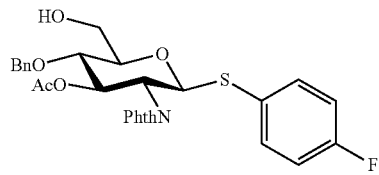

(2r)

[Chemical Formula 44]

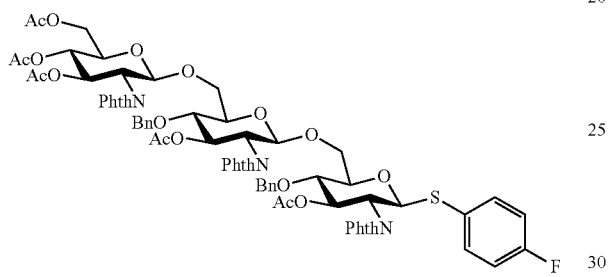

(3r)

As described above, the method for producing a glycan of this invention was found to improve yield ratio of streocontrolled glycan in liquid phase synthesis of oligosaccharide, as compared with the prior methods. In particular in glycan synthesis, in which a long glycan can be synthesized by repeating glycosylation that adds a sugar, yield ratio per cycle can largely affect the overall yield ratio when scaling up the glycan. Hence, this invention is particularly beneficial when such scaling-up is intended.

The invention claimed is:

1. A method for producing a glycan, the method comprising:
subjecting a building block A, which is at least one building block selected from a building block represented by Formula (1) below, or a building block that contains a sugar residue derived from the building block represented by Formula (1) below and a sugar residue derived from a building block represented by Formula (2) below, to electrolytic oxidation in an aprotic organic solvent that contains an electrolyte;
subjecting a building block B, which is at least one building block selected from a building block represented by Formula (2) below, or a building block that contains a plurality of sugar residues derived from the building block represented by Formula (2), to glycosylation with the electrolytically oxidized building block A; and
further repeating a sequence of the electrolytic oxidation and the glycosylation;
wherein the produced glycan is a polysaccharide equal to longer than trisaccharide;

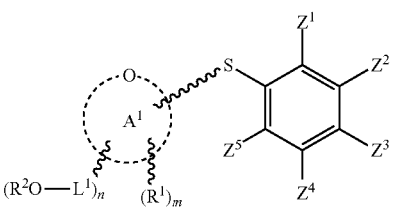

Formula (1)

in Formula (1),
$A^1$ represents a cyclic structure having 4 to 8 carbon atoms;
each of $Z^1$ to $Z^5$ independently represents a hydrogen atom or an electron attractive group, with the total of the Hammett's σ values of $Z^1$ to $Z^5$ exceeding 0.12;
$L^1$ represents a single bond or a divalent linking group;
each of $R^1$ and $R^2$ independently represents a monovalent organic group;
each of m ($R^1$)s and n ($R^2$)s may bind to each other to form a ring;
m represents an integer of 0 or larger, n represents an integer of 1 or larger;
m+n is equal to or smaller than the number of carbon atoms of the cyclic structure $A^1$;
each wavy line independently represents a bond in the equatorial or axial conformation;

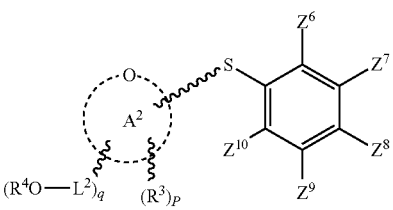

Formula (2)

in Formula (2),
$A^2$ represents a cyclic structure having 4 to 8 carbon atoms;
each of $Z^6$ to $Z^{10}$ independently represents a hydrogen atom or an electron attractive group, with the total of the Hammett's σ values of $Z^6$ to $Z^{10}$ exceeding 0.12;
$L^2$ represents a single bond or a divalent linking group;
$R^3$ represents a monovalent organic group,
$R^4$ represents a hydrogen atom or a monovalent organic group, at least one of q ($R^4$)s represents a hydrogen atom;
each of p ($R^3$)s and q ($R^4$)s may bind to each other to form a ring,
p represents an integer of 0 or larger, q represents an integer of 1 or larger;
p+q is equal to or smaller than the number of carbon atoms of the cyclic stricture $A^2$; and
each wavy line independently represents a bond in the equatorial or axial conformation,
wherein at least one of $Z^1$ to $Z^5$ represents chlorine atom, and
at least one of $Z^6$ to $Z^{10}$ represents chlorine atom.

2. The production method of claim 1, wherein the total of the Hammett's σ values of $Z^1$ to $Z^5$ is 0.2 or larger, with the total of the Hammett's σ values of $Z^6$ to $Z^{10}$ is 0.2 or larger.

3. The production method of claim 1, wherein the total of the Hammett's σ values of $Z^1$ to $Z^5$ is 1.5 or smaller, with the total of the Hammett's σ values of $Z^6$ to $Z^{10}$ is 1.5 or smaller.

4. The production method of claim 1, wherein any two of $Z^1$ to $Z^5$ represent chlorine atoms, and the other represent hydrogen atoms, and any two of $Z^6$ to $Z^{10}$ represent chlorine atoms, and the other represent hydrogen atoms.

5. The production method of claim 1, wherein one of $Z^1$ to $Z^5$ represents a chlorine atom, and the other represent hydrogen atoms, and one of $Z^6$ to $Z^{10}$ represents a chlorine atom, and the other represent hydrogen atoms.

6. The production method of claim 1, wherein a building block represented by Formula (1-2) below is used as the building block represented by Formula (1);

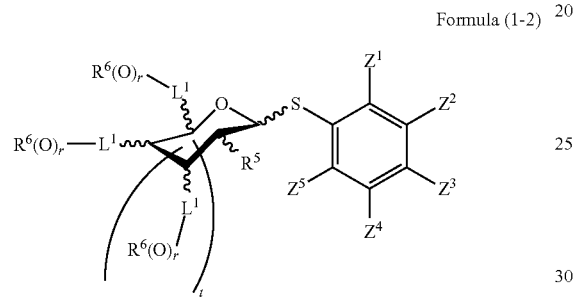

Formula (1-2)

in Formula (1-2), each of $Z^1$ to $Z^5$ independently represents a hydrogen atom or an electron attractive group, with the total of the Hammett's σ values of $Z^1$ to $Z^5$ exceeding 0.12;

each $L^1$ independently represents a single bond or a divalent linking group;

each of $R^5$ and $R^6$ independently represents a monovalent organic group;

$R^5$ and $R^6$ may bind to each other to form a ring, t represents an integer from 0 to 4;

each r independently represents 0 or 1; and each wavy line independently represents a bond in the equatorial or axial conformation;

wherein at least one of $Z^1$ to $Z^5$ represents chlorine atom, and at least one of $Z^6$ to $Z^{10}$ represents chlorine atom.

7. The production method of claim 6, wherein t represents 0 or 1.

8. The production method of claim 1, wherein a building block represented by Formula (2-2) below is used as the building block represented by Formula (2);

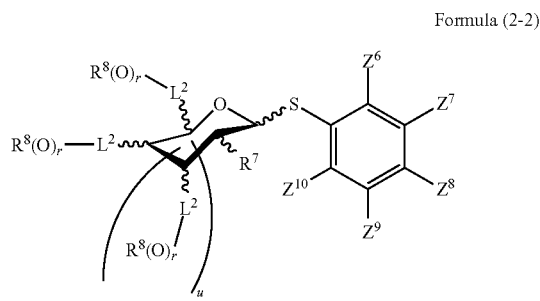

Formula (2-2)

in Formula (2-2), each of $Z^6$ to $Z^{10}$ independently represents a hydrogen atom or an electron attractive group, with the total of the Hammett's σ values of $Z^6$ to $Z^{10}$ exceeding 0.12;

$R^7$ represents a monovalent organic group, each $R^8$ independently represents a hydrogen atom or a monovalent organic group;

$R^7$ and $R^8$ may bind to each other to form a ring, u represents an integer from 0 to 4;

each r independently represents 0 or 1;

at least one $R^8(O)_r$ represents a hydroxy group; and each wavy line independently represents a bond in the equatorial or axial conformation;

wherein at least one of $Z^1$ to $Z^5$ represents chlorine atom, and at least one of $Z^6$ to $Z^{10}$ represents chlorine atom.

9. The production method of claim 8, wherein u represents 0 or 1.

10. The production method of claim 1, wherein $R^2$ is a protective group for hydroxy group, and $R^4$ other than a hydrogen atom is a protective group which is the same as the protective group as $R^2$.

11. The production method of claim 1, wherein $Z^3$ and $Z^8$ are chlorine atom.

12. The production method of claim 1, wherein building block A and building block B are monosaccharide.

13. The production method of claim 1, wherein one of $Z^1$ to $Z^5$ represents chlorine atom, and the other represent hydrogen atoms, one of $Z^6$ to $Z^{10}$ represents chlorine atom, and the other represent hydrogen atoms, and $Z^3$ and $Z^8$ are chlorine atom.

* * * * *